US007606274B2

(12) United States Patent  
Mirov et al.

(10) Patent No.: US 7,606,274 B2
(45) Date of Patent: Oct. 20, 2009

(54) MID-IR INSTRUMENT FOR ANALYZING A GASEOUS SAMPLE AND METHOD FOR USING THE SAME

(75) Inventors: Sergey Mirov, Birmingham, AL (US); Vladimir Fedorov, Birmingham, AL (US); Igor Moskalev, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 159 days.

(21) Appl. No.: 11/375,601

(22) Filed: Mar. 13, 2006

(65) Prior Publication Data

US 2007/0064748 A1 Mar. 22, 2007

Related U.S. Application Data

(60) Continuation-in-part of application No. 11/140,271, filed on May 27, 2005, which is a division of application No. 10/247,272, filed on Sep. 19, 2002, now Pat. No. 6,960,486.

(60) Provisional application No. 60/776,242, filed on Feb. 23, 2006, provisional application No. 60/774,952, filed on Feb. 17, 2006, provisional application No. 60/323,551, filed on Sep. 20, 2001.

(51) Int. Cl.
 *H01S 3/10* (2006.01)
(52) U.S. Cl. .............................. 372/20; 372/23; 372/10; 372/12
(58) Field of Classification Search .............. 372/10–17, 372/20, 23
 See application file for complete search history.

(56) References Cited

U.S. PATENT DOCUMENTS

| 4,158,207 | A |   | 6/1979  | Bishop et al. |
| 4,557,603 | A | * | 12/1985 | Oehler et al. ............... 356/418 |
| 4,847,138 | A |   | 7/1989  | Boylan et al. |
| 4,965,803 | A | * | 10/1990 | Esterowitz et al. ............ 372/5 |
| 5,461,635 | A |   | 10/1995 | Basiev et al. |
| 5,488,626 | A |   | 1/1996  | Heller et al. |
| 5,541,948 | A |   | 7/1996  | Krupke et al. |
| 5,671,241 | A | * | 9/1997  | Stamm et al. ................ 372/20 |
| 5,786,094 | A |   | 7/1998  | Kiuchi et al. |
| 5,832,008 | A |   | 11/1998 | Birnbaum et al. |
| 5,833,818 | A |   | 11/1998 | Townsend et al. |
| 5,867,305 | A | * | 2/1999  | Waarts et al. .......... 359/337.12 |

(Continued)

FOREIGN PATENT DOCUMENTS

WO   WO 2005/003845   1/2005

OTHER PUBLICATIONS

Wagner et al., "Continuous-wave broadly tunable CR2+:ZnSe laser," Opt. Lett. 24, 19-21 (1999).*

(Continued)

*Primary Examiner*—Minsun Harvey
*Assistant Examiner*—Xnning Niu
(74) *Attorney, Agent, or Firm*—Fish & Richardson P.C.

(57) ABSTRACT

An optical nose for detecting the presence of molecular contaminants in gaseous samples utilizes a tunable seed laser output in conjunction with a pulsed reference laser output to generate a mid-range IR laser output in the 2 to 20 micrometer range for use as a discriminating light source in a photoacoustic gas analyzer.

12 Claims, 12 Drawing Sheets

U.S. PATENT DOCUMENTS

| | | | |
|---|---|---|---|
| 6,236,666 | B1 | 5/2001 | Mirov et al. |
| 6,297,179 | B1 | 10/2001 | Beall et al. |
| 2004/0112278 | A1 | 6/2004 | Yoshida et al. |
| 2006/0050749 | A1 | 3/2006 | Setzler |

OTHER PUBLICATIONS

C. Sirtori, J. Faist, F. Capasso, D.L. Sivco, A.L. Hutchinson, A.Y. Cho, "Mid-Infrared (8.5 µm) Semiconductor Lasers Operating at Room Temperature", IEEE Photonics Technology Letters. 9/3, 294-296 (1997).

Y.H. Zhang, "Continuous wave operating of InAs/InAsxSb1-x midinfrared lasers" applied Physics letters 66 (2), 118-120 (1995).

F. Capasso et.al. "New Frontiers in Quantum Cascade Lasers and Applications", IEEE J. Select. Topics Quant. Elect. 6, 931 (2001) and references therein.

R. Colombelli et.al., "Far-infrared surface-plasmon quantum-cascade lasers at 21.5 µm and 24 µm wavelengths", Appl. Phys. Letters 78/18 2620-2622 (2001).

K. Vodopyanov; "Pulsed Mid-IR Optical Parametric Oscillators" in: Solid State Mid-Infrared Laser Sources, edited by I.T. Sorokina and K. L. Vodopyanov.(Springer-Verlag, Berlin Heidelberg, Topics in Applied Physics, ISSN 0303-4216; v. 89, 2003), pp. 141-178.

M. Ebrahimzadeh, "Mid-Infrared Ultrafast and Continuous-Wave Optical Parametric Oscillators" in: Solid State Mid-Infrared Laser Sources, edited by I.T. Sorokina and K.L. Vodopyanov (Springer-Verlag, Berlin Heidelberg, Topics in Applied Physics, ISSN 0303-4216; v. 89, 2003), pp. 179-218.

C. Fisher, M.W. Sigrist, "Mid-IR Difference Frequency Generation" in: Solid State Mid Infrared Laser Sources, edited by I.T. Sorokina and K.L. Vodopyanov (Springer-Verlag, Berlin Heidelberg, Topics in Applied Physics, ISSN 0303-4216; v. 89, 2003), pp. 97-140.

W.F. Krupke, R.H. Page, L.D. DeLoach, S.A. Payne, "Transition-Metal Doped Sulfide, Selenide, and Telluride Laser Crystal and Lasers", US Patent #5,541,948 (1996).

L.D. DeLoach, R.H. Page, G.D. Wilke, S.A. Payne, and W.F. Krupke, "Transition Metal-Doped Zinc Chalcogenides: Spectroscopy and Laser Demonstration of a New Class of Gain Media", IEEE J. Quatum Electron 32/6 885-895 (1996).

R.H. Page, K.I. Schaffers, L.D. DeLoach, G.D. Wilke, F.D. Patel, J.B. Tassano, S.A. Payne, W.F. Krupke, K.T. Chen, A. Burger, "Cr2+-Doped Zinc Chalcogenides as Efficient, Widely Tunable Mid-Infrared Lasers", IEEE J. Quantum Electron 33/4 609-617 (1997).

A. Fazzio, M.J. Caldas, and Alex Zunger, "Many-electron multiple effects in the spectra of 3d impurities in heteropolar semiconductors", Phys. Rev. B 30/6, 3430-3455 (1984).

W.F.Krupke, "Materials for lasers and nonlinear optics" in Advances in Lasers and Applications, Proceedings of the Fifty Second Scottish Universities Summer School in Physics, Sep. 1998, D.M.Finlayson and B.D.Sinclair Eds., SUSSP Publications & Institute of Physics Publishing, 1998.

K. Graham, S.B. Mirov, V.V. Fedorov, M.E. Zvanut, A. Avanesov, V. Badikov, B. Ignat'ev, V. Panutin, G. Shevirdyaeva, "Spectroscopic Characterization and Laser Performance of Diffusion Doped Cr2+:ZnS", OSA Trends in Optics and Photonics vol. 50, Advanced Solid-State Lasers, C. Marshall, Ed. (Optical Society of America, Washington, DC 2001) pp. 561-567.

K.Graham, S.B.Mirov, V.V.Fedorov, M.E.Zvanut, A.Avanesov, V.Badikov, B.Ignat'ev, V.Panutin, G.Shevirdyaeva, "Spectroscopic characterization and laser performance of diffusion doped Cr2+:ZnS", OSA Trends in Optics and Photonics vol. 34, Advanced Solid State Lasers, H.Injeyan, U.Keller and C.Marshall, eds. OSA Technical Digest (Optical Society of America, Washington DC, 2001), pp. 368-370 / WB 12-1 - 12-3.

K. Graham, S. Mirov, V. Fedorov, M.E. Zvanut, A. Avanesov, V. Badikov, B. Ignatev, V. Panutin, G. Shevirdyaeva, "Laser performance of Cr2+ doped ZnS", in Solid State Lasers X, Richard Scheps, Editor, Proc. SPIE 4267, 81-88 (2001).

G. J. Wagner, T.J. Carrig, R. H. Page, K. I. Schaffers, J. 0. Ndap, X. Ma, A. Burger, "Continuous-wave broadly tunable Cr2+: ZnSe laser", Opt. Lett. 24/1, 19-21 (1999).

A.V. Podlipensky, V. G. Shcherbitsky, N. V. Kuleshov, V. I. Levchenko, V. N. Yakimovich, A. Diening, M. Mond, S. Kuck, G. Huber, "1W continuous-wave laser generation and excited state absorption measurements in Cr2+:ZnSe", OSA Trends in Optics and Photonics, Advanced Solid State Lasers, Hagop Injeyan, Ursula Keller, and Christopher Marshall, Eds 34, 201-206 (Optical Society of America, Washington, DC, 2000).

I.T. Sorokina, E. Sorokin, A. DiLieto, M. Tonelli, R. H. Page, K. I. Schaffers, "0.5 W efficient broadly tunable continuous-wave Cr2+:ZnSe laser", OSA Trends in Optics and Photonics, Advanced Solid State Lasers, Hagop Injeyan, Ursula Keller, and Christopher Marshall, Eds 34, 188-193 (Optical Society of America, Washington, DC, 2000).

A. Sennaroglu, A. O. Konca, C. R. Pollock, "Power Performance of a Continuous-Wave Cr2+:ZnSe Laser at 2.47µm", OSA Trends in Optics and Photonics, Advanced Solid State Lasers, Hagop Injeyan, Ursula Keller, and Christopher Marshall, Eds 34, 240-245 (Optical Society of America, Washington, DC, 2000).

T. J. Carrig, G. J. Wagner, A. Sennaroglu, J. Y. Jeong, C. R. Pollock, "Acousto-Optic Mode-Locking of a Cr2+:ZnSe laser", OSA Trends in Optics and Photonics, Advanced Solid State Lasers, Hagop Injeyan, Ursula Keller, and Christopher Marshall, Eds 34, 182-187 (Optical Society of America, Washington, DC, 2000).

G.J. Wagner and T.J. Carrig, "Power Scaling of Cr2+:ZnSe Lasers," OSA Trends in Optics and Photonics vol. 50, Advanced Solid State Lasers, Christopher Marshall, Ed. (Optical Society of America, DC 2001), pp. 506- 510.

A.V. Podlipensky, V.G. Shcherbitsky, N. V. Kuleshov, V.I. Levchenko, V.N. Yakimovich, M. Mond, E. Heumann, G. Huber, H. Kretschmann and S. Kuck, Efficient laser operation and continuous-wave diode pumping of Cr2+:ZnSe single crystals, Appl. Phys. B 72, 253-255 (2001).

E.Sorokin, I.T.Sorokina, "Room-temperature CW diode-pumped Cr2+:ZnSe laser", in Advanced Solid State Lasers, OSA Technical Digest (Optical Society of America, Washington DC, 2001), pp. 51-53 / MB11-1—MB 11-3.

U. Hommerich, X. WU, V. R. Davis, S. B. Trivedi, K. Grasza, R. J. Chen, S. Kutcher, "Demonstration of room-temperature laser action at 2.5 µm from Cr2+:Cdo.85Mn0.15Te", Opt. Lett. 22/15, 1180-1182 (1997).

J. McKay, D. Kraus, K. L. Schepler, "Optimization of Cr2+:CdSe for Efficient Laser Operation", OSA Trends in Optics and Photonics, Advanced Solid State Lasers, Hagop Injeyan, Ursula Keller, and Christopher Marshall, Eds. 34 218-224 (Optical Society of America, Washington, DC, 2000).

J.J.Adams, C. Bibeau, R.H. Page, S.A Payne, "Tunable laser action at 4.0 microns from Fe:ZnSe", in Advanced Solid State Lasers, OSA Technical Digest (Optical Society of America, Washington DC, 2001).

S.B. Mirov, V.V. Fedorov, K. Graham, I. S. Moskalev, V.V. Badikov, V. Panutin, "Mid-IR Cr2+:ZnS and ZnSe Microchip Lasers", OSA vol. 68, Advanced Solid State Lasers, Martin E. Fermann and Larry R. Marshall, eds. (Optical Society of America, Washington DC, 2002), pp. 364-370.

S.B. Mirov, V.V. Fedorov, (Nov. 1, 2005) "Mid-IR Microchip Laser: ZNS:CR2+ Laser with Saturable Absorber Material", US Patent No. 6,960,486 B2.

I.T.Sorokina, E.Sorokin, S.B.Mirov, V.V.Fedorov, V.Badikov, V.Panyutin, A.DiLieto, M.Tonelli, "Continuous-wave tunable Cr2+:ZnS laser", Applied Physics B 74, 607-611(2002).

S. Mirov, V.V. Fedorov, K. Graham, I. Moskalev, V.V. Badikov, V. Panutin, "CW and pulsed Cr2+:ZnS and ZnSe microchip lasers," in OSA Trends in Optics and Photonics vol. 73, Conference on Lasers and Electro-Optics, OSA Technical Digest, Postconference Edition (OSA, Washington, DC, 2002), pp. 120-121.

I.T. Sorokina, E. Sorokin, S. Mirov, V. Fedorov, V. Badikov, V. Panyutin, "Broadly tunable compact continuous-wave Cr2+:ZnS laser", Optics Letters, 27/12, 1040-1042 (2002).

I.T. Sorokina, E. Sorokin, S. Mirov, V. Fedorov, V. Badikov, V. Panyutin, "Broadly tunable continuous-wave Cr2+:ZnS laser", in OSA Trends in Optics and Photonics (TOPS) vol. 73, Conference on Lasers and Electro-Optics, OSA Technical Digest, Postconference Edition (OSA, Washington DC, 2002), pp. 118-119.

S. B. Mirov, V. V. Fedorov, K. Graham, I. S. Moskalev, V. V. Badikov, V. Panyutin, "Erbium fiber laser-pumped continuous-wave microchip Cr2+:ZnS and Cr2+:ZnSe lasers", Optics Letters, 27/11, 909-911 (2002).

S.B. Mirov, V.V. Fedorov, K. Graham, I. S. Moskalev, I.T. Sorokina, E. Sorokin, V. Gapontsev, D. Gapontsev, V.V. Badikov, and V. Panyutin "Diode and fibre pumped Cr2+:ZnS mid-infrared external cavity and microchip lasers", IEE Proc.-Optoelectronics, 150 (4), 340-345 (2003).

I.S. Moskalev, V.V. Fedorov, S.B. Mirov, Multiwavelength mid-IR spatially-dispersive CW laser based on polycrystalline Cr2+:ZnSe, Optics Express 12 (20), 4986-4992 (2004).

J. Kernal, V. V. Fedorov, A. Gallian, S. B. Mirov, V. V. Badikov, "3.9-4.8 µm gain-switched lasing of Fe:ZnSe at room temperature", Optics Express 13 (26), 10608-10615 (2005).

V.V. Fedorov, S.B. Mirov, A. Gallian, D. V. Badikov, M.P. Frolov,Y.V. Korostein, V.I. Kozlovsky, A.I. Landman, Y.P. Podmar'kov, V.A. Akimov, A.A. Voronov, "3.77-5.05-µm Tunable Solid-State Lasers on Fe2+-Doped ZnSe Crystals Operating at Low and Room Temperatures", IEEE J. of Quantum Electronics 42(9), 907-917 (2006).

N. Riehl and H. Ortman, Z. Phys.Chem.A (109) 1941.

G.Grebe and H.J.Schulz,"Luminescence of Cr2+ Centres and Related Optical Interactions Involving Crystal Field Levels of Chromium Ions in Zinc Sulfide", Z. Naturforsch 29a, 1803-1818 (1974).

A.Zakrzewski and M. Godlewski, "Isolated iron and chromium recombination centers in ZnS", J. Appl. Phys. 67(5), 2457-2461 (1990).

M. Godlewski, A.J. Zakrzewski, V. Yu. Ivanov, "Auger-type excitation and de-excitation processes in rare-earth and transition metal doped semiconductors", J. of Alloys and Compounds, 300-301, 23-31 (2000).

M. Surma and M. Godlewski,"Nonradiative Recombination Processes in Wide Band Gap II-VI Phosphor Materials", Radiation Effects and Defects in Solids, 135, 213-216 (1995).

M. Godlewski, M. Kaminska, "The chromium impurity photogeneration transitions in ZnS, ZnSe and ZnTe", J. Phys. C: Solid St. Phys., 13, 6537-6545 (1980).

B.M. Kimpel, K. Lobe, H.J. Schulz, and E. Zeitler, "Generation of near-infrared light pulses from ZnS:Cr under laser-enhanced cathode-beam excitation", Measurement Science and Technology 6, 1383-1388 (1995).

G. O. Muller, in Solid State Luminescence, edited by A. H. Kitai (Chapman & Hall), London, 1993, p. 138.

G. Scamarcio, F. Capasso, A. L. Hutchinson, T. Tanbun-Ek, D. Sivco and A.Y. Cho, "Narrow-band electroluminescence at 3.5 µm from impact excitation and ionization of Fe2+ ions in InP", App. Phys. Lett. 68 (10), 1374-1376 (1996).

P.B.Kleinm J.E.Furneaux, and R.L.Henry, "Laser oscillation at 3.53 µm from Fe 2+ in n-InP:Fe", Appl. Phys. Lett. 42(8) 638-640 (1983).

V.Y. Ivanov, M. Godlewski, T.P. Surkova, N. Zhavoronkov, A.R. Omelchuk, "Blue Anti-Stokes Emission in Chromium and Iron Doped Wide Band Gap II-VI Compounds", Phys. Stat. Sol. (b) 229, No. 1, 355-359 (2002).

J.C. Bouley, P. Blanconnier, A. Herman, Ph.Ged, P. Henoc, J.P. Noblanc, "Luminescence in highly conductive n-type ZnSe", J. App. Phys. 46 (8), 3549-3555 (1975).

V.A. Kasiyan, R.Z. Shneck, Z.M. Dashevsky, and S.R. Rotman, "Development of All-BVI Semiconductors Doped with Cr for IR Laser Application", Phys. Stat. Sol. (b) 229, 395-398 (2002).

R.G. Kaufman, P. Dowbor, "Mechanism of formation of Ohmic contacts to ZnSe, ZnS, and mixed crystals ZnSxSe1-x", J. Appl. Phys., 45 (10), 4487-4490, (1974).

R.N. Bhargava, D. Gallagher, X. Hong, A. Nurmikko, "Optical Properties of Manganese-Doped Nanocrystals of ZnS", Phys. Rev. Lett. 72(3), 416-419 (1994).

M. Tanaka, "Photoluminescence properties of Mn2+- doped II-VI semiconductor nanocrystals", J. of Luminescence 100, 163-173 (2002).

V.I. Klimov, A.A. Milkhailovsky, Su Xu, A. Malko, J.A. Hollingsworth, C.A. Leatherdale, H.-J. Eisler, M.G. Bawendi, Optical Gain and Stimulated Emission in Nanocrystal Quantum Dots, Science, 290, 314-317, 2000.

M. Klude, T. Passow, R. Kroger, and D. Hommel, "Electrically pumped lasing from CdSe quantum dots", Electron. Lett. 37(18), 1119-1120 (2001).

A.P. Alivisatos, "Semiconductor Clusters, Nanocrystals, and Quantum Dots", Science 271(5251), 933-937(1996).

C.B. Murray, D.J. Norris, and M.G. Bawendil, "Synthesis and Characterization of Nearly Monodisperse CdE (E = S, Se, Te) Semiconductor Nanocrystallites", J. Am. Chem. Soc., 115, 8706-8716, (1993).

R.N. Bhargava, "Quantum-confined atoms": novel luminescent centers for future II-VI devices, J. Crystal Growth, 214/215, 926-930 (2000).

B A. Smith , J.Z. Zhang, A. Joly, J. Liu, "Luminescence decay kinetics of Mn2+–doped ZnS nanoclusters grown in reverse micelles", Phys. Rev. B, 62(3), 2021-2028 (2000).

W. Chen, R. Sammynaiken, Y. Huang, "Luminescence enhancement of ZnS:Mn nanoclusters in zeolite", J. Appl. Phys., 88(9), 5188-5193 (2000).

K. Katayama, H. Matsubara, F. Nakanishi, T. Nakamura, H. Doi, A. Saegusa, T. Mitsui, T. Matsuoka, M. Iirikua, T. Takebe, S. Nishine, T. Shirakawa, "ZnSe-based white LEDs", Journal of Crystal Growth 214/215, 1064-1070 (2000).

C. Boney, Z. Yu, W.H. Rowland, Jr., W.C. Hughes, J.W. Cook, Jr., J.F.Schetzina, G. Cantwell, and W.C. Harsch, "II-VI blue/green laser diodes on ZnSe substrates", J. Vac. Sci. Technol. B 14(3), 2259-2262 (1996).

H. Okuyama, K. Nakano, T. Miyajima and K. Akimoto, "Epitaxial Growth of ZnMgSSe on GaAs Substrate by Molecular Beam Epitaxy", Japanese J. Appl. Phys. 30(9B), L1620-L1623 (1991).

J.M. Gaines, R.R. Drenten, K.W. Haberern, T. Marshall, P. Mensz, J. Petruzzello, "Blue-green injection lasers containing pseudomorphic Zn1-xMgxSySe1-y cladding layers and operating up 394 K ", Appl. Phys. Lett., 62(20), 2462-2464 (1993).

M.A. Haase, P.F. Baude, M.S. Hagedorn, J. Qiu, J.M. DePuydt, H. Cheng, S. Guha, G.E. Hofler and B.J. Wu, "Low-threshold buried-ridge II-VI laser diodes", Appl. Phys. Lett. 63(17) 2315-2317 (1993).

A. Ishibashi, "II-VI blue-green light emitters", Journal of Crystal Growth 159, 555-565 (1996).

F.T. Quinlan, J. Kuther, W. Tremel, W. Knoll, S. Risbud and P. Stroeve, "Reverse Micelle Synthesis and Characterization of ZnSe Nanoparticles", Langmuir 16, 4049-4051 (2000).

S. Wage, Z. S. Ling, Xu Xu-Rong, "Growth and optical properties of colloidal ZnS nanoparticles", J. Crystal Growth 255, 332-337 (2003).

M. Epifani, G. Leo, M. Lomascolo and L. Vasanelli, "Sol-Gel Synthesis of Hybrid Organic-Inorganic Monoliths Doped with Colloidal CdSe/ZnS Core-Shell Nanocrystals", J. Sol-Gel Sci. and Technol. 26, 441-446 (2003).

V. Stanic, T.H. Etsell, A.C. Pierre, R.J. Mikula, "Sol-gel processing of ZnS", Materials Letters 31, 35-38 (1997).

G.N. Karanikolos, P. Alexandridis, G. Itskos A. Petrou and T.J. Mountziaris, "Synthesis and Size Control of Luminescent ZnSe Nanocrystals by a Microemulsion-Gas Contacting Technique", American Chem. Society.

S.L. Cumberland, K.M. Hanif, A. Javier, G.A. Khitrov, G.F. Strouse, S.M. Woessner and C.S. Yun, "Inorganic Clusters as Single-Source Precursors for Preparation of CdSe, ZnSe, and CdSe/ZnS Nanomaterials", Chem. Matter., 14, 1576-1584 (2002).

B. Bhattacharjee, D. Ganguli, S. Chaudhuri, A.K. Pal, "ZnS:Mn nanocrystallites in SiO2 matrix: preparation and properties", Thin Solid Films 422, 98-103 (2002).

K.V. Anikin, N. N. Melnik, A.V. Simakin, G.A. Shafeev, V.V. Voronov, A.G. Vitgukhnovsky, "Formation of ZnSe and CdS quantum dots via laser ablation in liquids", Chem. Physics Letters 366, 357-360 (2002).

T. Sasaki, Y. Shimizu, N. Koshizaki, "Preparation of metal oxide-based nanomaterials using nanosecond pulsed laser ablation in liquids", J. Photochemistry and Photobiology A: Chemistry 182, 335-341 (2006).

V.T. Liver, M. Rossi, G. D'Arrigo, D. Manno, G. Micocci, "Synthesis and characterization of ZnS nanoparticles in water / AOT / n-heptane microemulsions", Appl. Phys. A 69, 369-373 (1999).

* cited by examiner

Diode pumped Er fiber laser

| Crystal | Transparency range (μm) | n | $d_{\text{eff}}$ | FOM |
|---|---|---|---|---|
| PPLN | 0.4-5.5 | 2.1 | ~22 | 1 |
| ZGP | 2-12 | 3.1 | ~75 | 8.8 |
| CdSe | 0.8-21 | 2.5 | ~18 | 0.4 |
| GaSe | 0.7-20 | 2.7 | ~55 | 3.9 |
| $AgGaSe_2$ | 0.8-16 | 2.6 | ~25 | 0.6 |

Figure 6

Figure 11. Transmission spectrum of ZGP crystal over 500-3000 nm spectral range. It shows that current technology of after growth crystals treatment allows decreasing residual absorption of the ZGP crystal at wavelength > 1.6 μm and utilization of Er:YAG laser (1.65 μm) as a pump source for ZGP based OPG.

MID-IR INSTRUMENT FOR ANALYZING A GASEOUS SAMPLE AND METHOD FOR USING THE SAME

CROSS REFERENCE TO RELATED PATENT APPLICATIONS

This patent application claims priority from U.S. Provisional Patent Application No. 60/774,952, filed on Feb. 17, 2006, and from U.S. Provisional Patent Application No. 60/776,242, filed on Feb. 23, 2006, and is further a continuation-in-part of U.S. patent application Ser. No. 11/140,271, filed on May 27, 2005, which is a divisional application of U.S. patent application Ser. No. 10/247,272, which was filed on Sep. 19, 2002 and issued as U.S. Pat. No. 6,960,486, which claimed priority from U.S. Provisional Patent Application No. 60/323,551, filed on Sep. 20, 2001, each of these references being incorporated herein by reference.

The U.S. Government has a paid-up license in this invention and the right in limited circumstances to require the patent owner to license others on reasonable terms as provided for by the terms of Contract/Grant No. BES-0521036 awarded by NSF.

FIELD OF THE INVENTION

The present invention relates to the field of Quantum Electronics, and more particularly to the elemental basis of laser technology, and can be used to develop tunable mid-infrared (mid-IR) solid state lasers.

More specifically, the invention can be used in cases where monochromatic laser emission tunable in the middle-infrared spectral region is required for solving problems in various fields of science and technology, such as laser spectroscopy, trace gas analysis, photo chemistry, photo biology, medicine, and wavelength specific military applications, among others.

Even more specifically, the present invention is an instrument that is capable of analyzing a given gaseous sample with a full chemical specificity, with ultimate sensitivity, and real time speed.

Even more particularly, the present invention relates to instrumentation that is able to measure biomarkers for early diagnosis and management of diseases.

BACKGROUND OF THE INVENTION

There is a growing demand for affordable mid-infrared sources for use in a variety of applications including eye-safe medical laser sources for non-invasive medical diagnostics, eye-safe laser radar and remote sensing of atmospheric constituents, optical communication, and numerous military applications. These applications rely on the existence of "spectroscopic fingerprints" of numerous organic molecules in the mid-IR range of optical spectrum.

Such organic molecules play the fundamental role in numerous biochemical processes on a single cell level as well as in most other fields of life sciences, in environmental research, in industrial processes, and in global geo-physical processes. Hence, it is essential to detect the molecular content of a given sample with full chemical specificity, with ultimate sensitivity, and with real-time speed. For example, one such area where measuring a gas sample may be effective in addressing disease early is in identifying biomarkers for cancer. More specifically, lung cancer is the most common cause of cancer-related mortality in both men and women in the United States. An estimated 173,700 Americans will receive a diagnosis of lung cancer every year with 164,440 of them expected to die of the disease, a mortality rate of over 90%. Survival rates for lung cancer have changed little over the past twenty-five years despite years of research, which is because most lung cancers are diagnosed at an advanced stage when curative treatment is no longer possible. Identifying lung cancer at the earliest stage is central to improving outcomes; even a small decrease in lung cancer mortality from effective screening of high-risk individuals would save thousands of lives each year. However, current screening techniques, such as chest radiology, sputum cytology and chest CT scanning are insensitive or non-specific and are not recommended for use by the American Cancer Institute. It is for problems such as the detection of lung cancer that an instrument for identifying molecules is desired.

It has been widely accepted that optical detection, or an "optical nose," is the only approach that can meet the extreme demands for molecular detection. For ultimate performance, optical detection of molecules has to be performed in the so-called "molecular fingerprint region," located in the 2 and 20 µm mid-IR spectral range. In this region, all the important gas molecules possess dense series of strong, narrow-band absorption lines corresponding to rotational-vibrational transitions. By measuring the mid-IR light absorption of a gas sample, basically all compounds can be identified and their individual concentrations can be measured.

Despite the need for such molecule detection, this substantial potential of mid-IR optical detection of molecules cannot be realized with any of the currently existing laser sources and detection techniques. Consequently, progress in many research areas of life-sciences has been held back since such areas depend on a fast and complete analysis of gas samples. For advanced molecular detection, novel mid-IR laser sources must be developed that can measure molecules in gases and vapors which, at atmospheric pressure, have spectral features which are typically a few $0.1$ $cm^{-1}$ wide. At low pressures, where Doppler broadening dominates, these features can be even sharper: $<10^{-2}$ $cm^{-1}$. In this case, single-longitudinal-mode (SLM) lasers are desirable. In addition to this high spectral resolution, a high species selectivity and full profiling capability requires a maximum coverage of the molecular fingerprint spectral region (2-20 µm, see HITRAN database). For real time analysis, the novel laser sources have to provide good wavelength agility (hundred thousands of distinct wavelengths per second). Moreover, multiple envisioned practical applications of the designed instrument, including use in environmental monitoring, geo-physical exploration, counterterrorism (explosive detection), food production, and biomedicine (breath analysis for early diagnostics of diseases) dictate necessity of extremely high detection sensitivities, up to parts per trillion which, in turn, requires high power (Watt level) and low-noise sources.

Even after four decades of laser and nonlinear optical research, ideal versatile sources capable of generating the mid-IR radiation required for the envisioned applications do not exist. Previous attempts to utilize mid-IR laser sources, such as lead salt diode lasers, quantum cascade lasers, and free-electron lasers, suffered from their insufficient output power or spectral controllability, resulting in an unacceptably low detection sensitivity, selectivity and speed. So far, the most promising sources of coherent radiation for mid-IR optical nose are optical parametric oscillators (OPOs) that are powerful solid state sources of broadly tunable coherent radiation, capable of covering the entire spectral range from the near UV to the mid IR, and can operate from continuous wave (CW) down to the femtosecond pulse durations. OPOs are capable of generating coherent radiation at wavelengths where lasers perform badly or are unavailable. In the molecular fingerprint region of the optical spectrum, 2-20 µm, where we lack broadly tunable lasers, similar to dye lasers in the visible or titanium-doped sapphire (Ti—S) in the near infrared, the OPOs play a particularly important role.

Conventional continuous wave (cw), especially diode and fiber laser pumped OPOs are promising of being capable to deliver highest spectral purity of the output radiation in a compact set-up. However, such OPOs are restricted to wavelengths shorter than 5 µm and require utilization of single (SRO) and/or double resonant cavities (DRO) for significant threshold reduction. This has the consequence that the length of the OPO cavity should be precisely stabilized to the pump laser wavelength by piezoelectric transducer (PZT) control system that make very problematic fast and broad mode-hope free tuning of the system required for envisioned applications.

Conventional pulsed OPOs and optical parametric generators (OPGs) are promising, although their spectra are either difficult to control (ns OPOs), or too broad (ultrashort pulsed OPOs), or the average power is too low (OPGs). It is noteworthy that, even when novel proposed coherent mid-IR sources will be developed, the detection of their radiation poses further challenges. Fast photodiodes, photomultipliers and CCD cameras, readily available in the visible and near-IR, do not exist in the mid-IR. Hence, highly effective signal enhancement techniques such as cavity ring-down spectroscopy (CRDS), multipass, frequency modulation, and photoacoustic enhancement techniques will require special attention to be successfully implemented in the mid-IR.

SUMMARY OF THE INVENTION

The present invention provides instrumentation that is capable of analyzing a given gaseous sample with a full chemical specificity, with ultimate sensitivity, and with real time speed. The instrument is able to provide this analysis by applying optical detection methods based on high-power, ultra-broadly and rapidly tunable mid-IR sources and compatible sensing and signal enhancing techniques. Several components are combined into one system to realize such a high-power, ultra-broadly and rapidly tunable mid-IR source.

In particular, in order to overcome the limitations of existing sources of mid-IR radiation for advanced molecular detection, the present invention does not follow well known paths of research that lead either towards ever-shorter pulses with fs durations for a higher peak powers and temporal resolution, or towards ever-smaller milli-Hz bandwidths for higher spectral resolution and accuracy. Rather, the present invention is focused on the intermediate range of hundreds of ns—microsecond pulse durations providing sufficient spectral resolution for molecular detection and output powers much higher than in narrow-band CW systems.

To satisfy the requirements for rapid and very broad tunability, injection seeded $ZnGeP_2$ (ZGP) and CdSe OPG-optical parametric amplifier (OPA) scheme has been chosen. Since the OPG-OPA has no cavity modes, it amplifies a whole continuum of frequencies inside its phase-matching acceptance bandwidth, and there is no need of frequency mode matching between the seed and OPG-OPA modes. Consequently, a combination of SLM pump laser and the rapid (synchronously with nonlinear optical crystal) tuning of the SLM injection seeder (signal) will provide rapidly tuned SLM idler.

Resonantly Tm fiber laser cw-pumped, repetitively Q-switched Ho:YAG (2.09 µm) or YLF (2.05 µm) laser serves as an effective pump source of OPG-OPA system based on a high figure of merit (FOM) ZGP and CdSe nonlinear crystals. This approach of direct laser pumping (using ~1.9 µm) of the $^5I_7$ manifold of Ho ions featuring long fluorescence lifetime of 8-16 ms provides access to the high energy storage capability of Ho. Recently great potential of resonant Tm:YLF pumped Ho:YAG and Ho:YLF lasers has been demonstrated in research with Q-switched to normal-mode extraction efficiency of 100%, up to 82% overall quantum efficiency of lasing, yielding high average power levels (>20 W) with either low per pulse energies (~1 mJ) in the tens of kHz or 20 mJ at 1 kHz. A unique multi-Watt (>20 W), multi-mJ (>10 mJ) output capabilities of Ho:YAG/YLF—ZGP OPO combination has been also recently documented in research.

Alternatively, a resonantly Er fiber laser cw-pumped, repetitively Q-switched Er:YAG (1.65 µm) laser could also serve as an effective pump source of OPG-OPA system based on high figure of merit (FOM) ZGP nonlinear crystal. This approach of direct laser pumping (using ~1.53 µm) of the $^4I_{13/2}$ manifold featuring long fluorescence lifetime of 13 ms provides access to the high energy storage capability of Er.

SLM ultrabroadly (2-3.5 µm) tunable seed laser will be based on novel $Cr^{2+}$ doped ZnS, ZnSe or CdSe crystals. These media are very close mid-IR analogues of the (Ti—S). It is anticipated that, like the Ti—S laser, $TM^{2+}$ doped chalcogenides will be lasing with a great variety of possible regimes of oscillations, but with an additional significant advantage of being directly pumpable with radiation of InGaAsP diode lasers. During recent years, several groups[12-27], including the present applicants, actively explored analogous $TM^{2+}$ crystal hosts and have demonstrated efficient broadly tunable room temperature (RT) lasing in CW, free-running long pulse, gain switched and mode-locked regimes of operation.

Finally, $Cr^{2+}$-doped II-VI master oscillator-power amplifier (MOPA) system will be directly pumped by Tm- or Er-fiber laser. The same Tm- or Er-fiber laser will be also utilized for resonant excitation of the $^5I_7$ manifold of Ho, or $^4I_{13/2}$ manifold of Er lasers, respectively, and will serve as a single pump source for the overall system.

The instrument of the present invention is capable of identifying a large variety of molecules in multi-compound gas-mixtures and to quantify them at ultra-low concentration levels (parts per billion and lower). The instrument will provide a complete, total profile of the trace gas contents in complex gas mixtures in real-time, i.e. with response times in the order of seconds. In operation, the optical instrument functions initially by taking a sampling of the desired molecules. Molecules above the solution are delivered into optical cell. The tunable laser radiation then excites molecules in the cell. Interaction of light with molecules gives rise to characteristic absorption spectra, which are fed into a computer-based spectrum recognition algorithm. Molecules may then be identified and quantified.

BRIEF DESCRIPTION OF THE DRAWINGS

The herein described features of the present invention, as well as others which will become apparent, are attained and can be understood in more detail by reference to the following description and appended drawings, which form a part of this specification. It is to be noted, however, that the appended drawings illustrate only exemplary embodiments of the invention and therefore not be considered limiting of its scope, for the invention may admit other equally effective embodiments.

FIG. 6 is a table providing a comparison of major optical characteristics of nonlinear crystals with periodically poled lithium niobate (PPLN) crystal;

DESCRIPTION OF THE PREFERRED EMBODIMENT

Figure 1:
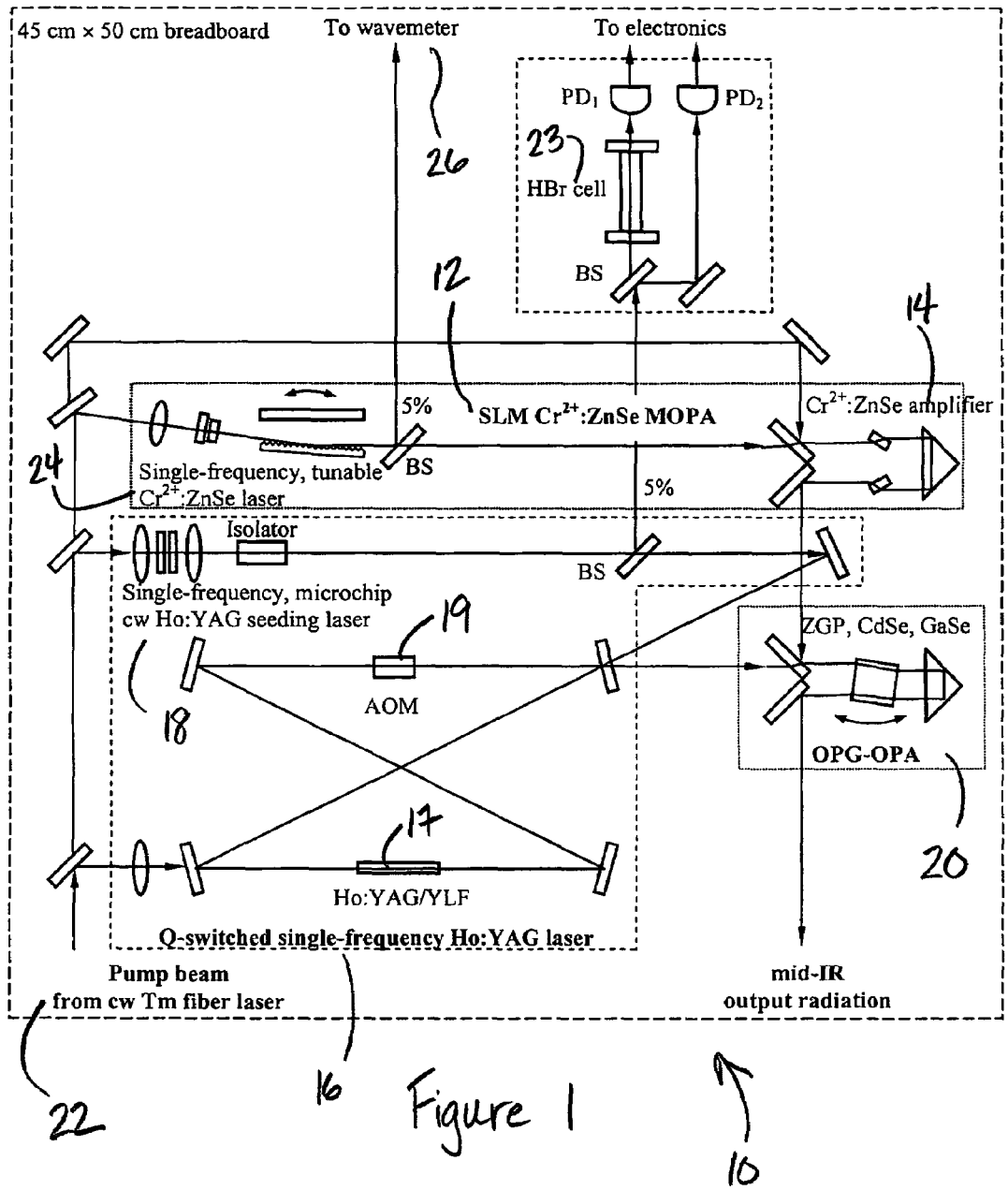
FIG. 1 is a schematic diagram of the optical nose instrument of the present invention.
Figure 2:
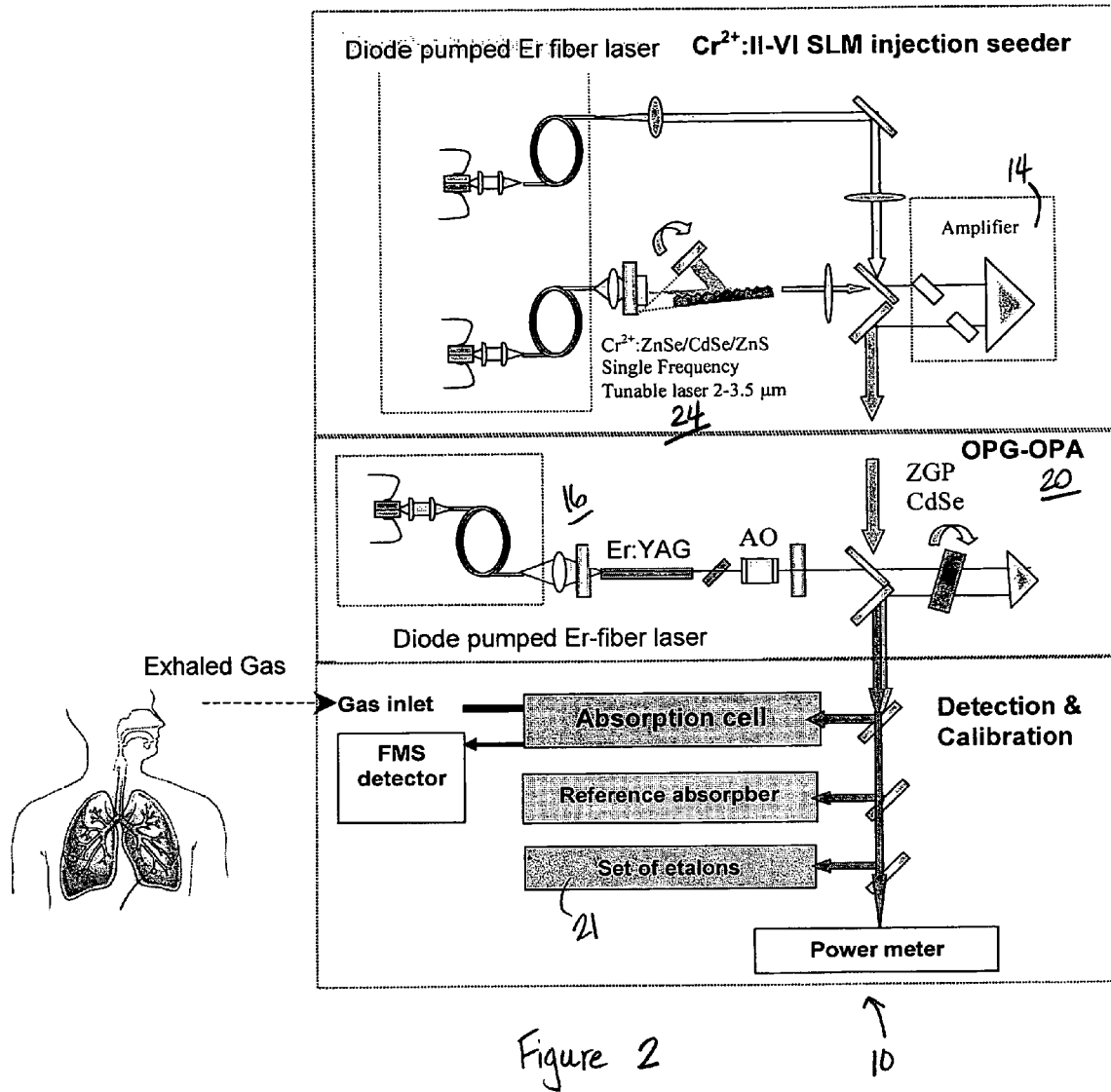
FIG. 2 is a block diagram of the optical nose instrument of the present invention.
Figure 3:
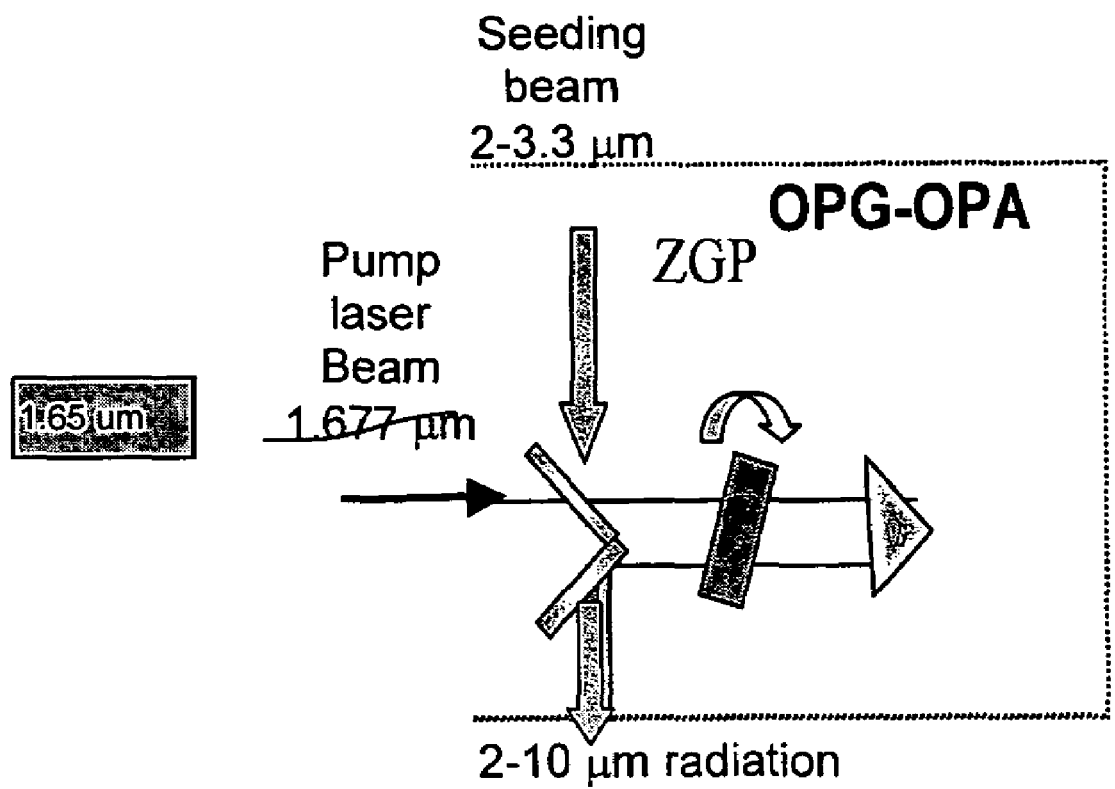
FIG. 3 is a block diagram of the OPG of the optical nose instrument illustrated in FIG. 2.

Looking to FIGS. 1 and 2, the present invention involves two main areas of instrumentation, namely laser and nonlinear optics, and optical detection and signal enhancement methods. These aspects of tunable infrared laser spectroscopy have been of great interest to researchers for many years and are comprehensively reviewed by Curl and Tittel (see 56 and 628 references herein).

Development of advanced molecular detection instrument, capable of analyzing gaseous sample in real time with full chemical specificity and ultimate sensitivity, requires development of novel mid-IR laser sources with very challenging properties: SLM regime of operation, ultrabroad continuous tunability over the molecular fingerprint of 2-20 μm, good wavelength agility, high power (watt level), and low noise. Analysis of available mid-IR laser sources, such as tunable solid state lasers, antimonite and lead salt diode lasers, quantum cascade lasers, line tunable gas lasers, free electron lasers, OPOs and OPGs, show that all these sources suffer from either insufficient output power, or spectral controllability resulting in poor detection sensitivity, selectivity, and speed. So far, the most promising sources of coherent radiation for proposed optical nose spectrometer are OPOs or OPGs, capable of generating coherent radiation at wavelengths where lasers perform poorly or unavailable. To satisfy the requirements for rapid, narrow linewidth and ultrabroad tunability, injection seeded ZGP and CdSe or GaSe OPG-OPA scheme has been chosen. For the reason that OPG-OPA has no cavity modes, it amplifies a whole continuum of frequencies inside its phase-matching acceptance bandwidth, and there is no need of frequency mode matching between the seed and OPG-OPA modes.

In terms of operation, the inventors aim at a largely unexplored intermediate range of submicro-microseconds pulse durations (quasi-continuous wave, qcw) that provides sufficient spectral resolution for molecular detection and output powers orders of magnitude higher than in cw systems. Compared to short pulsed (ns, ps, fs) OPOs and OPGs, the moderate peak powers of qcw devices (tens of Watts) are supposed to prevent saturation effects, and their high duty cycles of ~$10^{-1}$ (conventional pulsed sources have $10^{-3}$ to $10^{-5}$) can significantly improve signal-to-noise ratio.

There is currently an increased interest towards the new class of the transition-metal ($TM^{2+}$) doped zinc chalcogenides, and in particular towards Cr:ZnSe, ZnS and CdSe as broadly tunable continuous-wave (CW) lasers operating at room temperature over 2-3.5 μm spectral range. This interest is explained by excellent laser properties of these materials as well as by the variety of possible applications, such as environmental analysis, remote sensing, spectroscopy and medicine. Several groups have actively explored analogous $TM^{2+}$ crystal hosts for tunable lasing in CW, free-running long pulse, gain switched and mode-locked regimes of operation. The most impressive results—room temperature operation, >60% lasing efficiency, 18 W of quasi-CW output power, more than 1100 nm range of tunability—have been obtained using $Cr^{2+}$:ZnSe crystals. Studies of our research group have resulted in optimized technology of two-stage ZnS, ZnSe, CdS, and CdSe crystals preparation. At the first stage, undoped single- or poly-crystals are synthesized by a chemical transport reaction from gas phase using iodine gas transport scheme. During the second stage introduction of chromium is performed by thermal diffusion from chromium thin film deposited by pulsed laser deposition (PLD) method on a thin wafer of II-VI material. Several impressive results have been recently obtained with these new crystals, including the following:

1) We developed the first continuous-wave, room-temperature, tunable over more than 280 nm at ~2.3 μm $Cr^{2+}$:ZnS laser, pumped with a Co:MgF$_2$ laser and yielding over 100 mW of output power[32].

2) Another key result is the first successful demonstration of CW $Cr^{2+}$:ZnS and ZnSe microchip lasers with the maximum output powers of 500 mW at 2320 and slope efficiency of 53% under direct (without coupling optics) Er-fiber laser excitation[31,36,37].

3) We also developed first gain switched $Cr^{2+}$:ZnSe microchip laser. A maximum slope efficiency of 6% and maximum output energy of 1 mJ were obtained for a microchip without mirrors, when positive feedback was due only to the Fresnel reflections[33,37].

4) First tunable, directly diode-pumped by two conventional 500 mW InGaAsP-InP telecom laser diodes CW $Cr^{2+}$:ZnS laser was also reported. Tunability over 400 nm between 2250 and 2650 nm was achieved.

5) In external cavity configuration, a compact Er-fiber laser pumped, broadly tunable over ~700 nm between 2170 and 2840 nm (potential tunability >1000 nm), CW, room-temperature $Cr^{2+}$:ZnS laser was realized, yielding up to 700 mW at ~40% slope efficiency.

6) Finally, first multiwavelength (40 lines), spatially dispersive CW $Cr^{2+}$:ZnSe laser has been reported.

Further optimization of these lasers and their utilization as broadly tunable seed lasers for ZGP OPG-OPA system will stimulate a number of new applications such as field-portable spectroscopy systems for scientific, commercial, medical, and military applications.

Looking to FIG. 2, as a major pump source for OPG-OPA combination, repetitively Q-switched solid state laser (e.g. Ho:YAG (2.09 μm) or YLF (2.05 μm) laser, or Er:YAG (1.65 μm)), resonantly pumped by a cw fiber or diode laser 22 (e.g. Tm or Er fiber laser or diode laser), has been chosen. This approach of direct laser pumping of the long-lifetime manifold (e.g. $^5I_7$ of Ho ion or $^4I_{13/2}$ manifold of Er ion) featuring long fluorescence lifetime of 8-16 ms provides access to the high energy storage capability of Ho and Er and provides, up to 80% overall quantum efficiency of lasing, yielding high average power levels (>20 W) with either low per pulse energies (~1 mJ) in the tens of kHz and several microsecond pulse durations or 20 mJ at 20 ns and 1 kHz. A unique multi-Watt (>20 W), multi-mJ (>10 mJ) output capabilities of Ho:YAG/YLF—ZGP OPO combination have been recently documented.

Single longitudinal mode (SLM) ultrabroadly tunable (2-3.5 μm) seed laser and power amplifier of the present invention is based on the novel class of $Cr^{2+}$ doped ZnS, ZnSe or CdSe crystals, wherein the present inventors have developed a significant expertise in technology and applications of these unique mid-IR analogs of Ti—S laser.

A block diagram of optical nose system 10 having a broadly tunable, narrow linewidth mid-IR laser source is depicted in FIG. 1. The laser source has a modular structure and consists of the following three major components: 1) Single-longitudinal mode, widely tunable $Cr^{2+}$:ZnSe master oscillator 12 with a $Cr^{2+}$:ZnSe power amplifier 14; 2) Single-frequency, high energy, Q-switch Ho:YAG/YLF laser 16 with a single-longitudinal mode, frequency-stabilized injection-seeding laser 18; 3) Optical Parametric Amplifier 20. This laser unit will be the basic unit of the optical nose system. All lasers of the laser unit, and the $Cr^{2+}$:ZnS/ZnSe amplifier 14, will be pumped by a single cw (e.g. 40 W) Tm fiber laser 22.

There are generally two reliable and convenient approaches in developing a high energy, single-frequency, Q-switched laser systems. Both approaches are based on injection-seeding of the pulsed laser by a low-power, narrow-linewidth, and frequency-stabilized cw laser. The first approach is based on the use of a relatively compact linear standing-wave laser cavity and an electro-optic modulator (EOM) Q-switch. Such construction is used in a number of commercially available single-mode pulsed laser systems, e.g. the GCR-230 Nd:YAG laser. However, for the 2-3 μm spectral region, the only material commercially available for EOM is $LiNbO_3$, which has a relatively low damage threshold. The latter will lead to a reduced reliability of the Ho-laser at high output energies required for the mid-IR laser source for the optical nose system. For these reasons, we have chosen an alternative laser scheme, which is based on a ring laser resonator and an acousto-optic Q-switch. This type of laser technology has shown pulse energy as high as 600 mJ with a single-frequency output spectrum.

Continuing to view FIG. 1, the 40 mm-long Ho:YAG or YLF rod 17 (mounted on thermoelectrically cooled copper finger) doped with 0.5% of holmium and positioned in the ring cavity will be resonantly pumped directly to the $^5I_7$ manifold by the radiation of the Tm-fiber laser 22. A Brewster-cut acousto-optic modulator (AOM) 19 will be used to Q-switch the Ho-laser featuring high energy storage capability. It is envisioned that the present invention will obtain up to 20 W of output power for CW Ho-laser, approximately 10 mJ and 1000 Hz in the Q-switched regime with approximately 100 ns pulse durations, and approximately 1 mJ and 10000 Hz with 1-1.5 μs pulse durations.

In order to obtain a single-frequency operation of the Q-switched Ho:YAG/YLF laser 17, a single-longitudinal-mode, low-power (~10 mW), frequency stabilized Ho:YAG injection seeding laser, pumped by cw Tm-fiber laser 22, is used. As the basic scheme of the injection seeding laser, a microchip configuration with a PZT-tunable external etalon 21 is used. The absolute frequency stabilization will be achieved by locking the laser frequency to the P(12) absorption line of the HBr molecule 23 at 2097.2 nm. This technique will allow for obtaining long-term frequency stability and single mode operation of cw Ho:YAG laser 16 for injection seeding of Q-switch Holmium laser.

The $Cr^{2+}$:ZnSe/CdSe/ZnS master oscillator-power amplifier 14 will now be discussed. Various schemes of the grating cavity (Littrow or Littman schemes) are in wide use in dye lasers, Ti:S lasers, diode lasers, and other types of tunable lasers. The main advantages of the grazing incidence grating cavity are high spectral selectivity, simple construction, and ease of control. A smooth tuning of oscillation frequency without mode hops is an important task for tunable single frequency laser design. Analysis of this problem has been performed in references. It has been shown that smooth tuning might be achieved by optimization of the position for the diffraction grating's axes of rotation. In several publications smooth tuning ranges of 15 nm and 82 nm has been demonstrated for external cavity diode lasers operating at 1260 and 1540 nm wavelengths, respectively. The continuous tuning range increases at larger wavelengths, so we estimated that continuous mode-hope-free tuning for $Cr^{2+}$ master oscillator laser might exceed 150 nm. Remarkably narrow linewidth (less than 600 MHz) of the $Cr^{2+}$:ZnSe laser has been sustained in the report. In the long-term, stability measurements of the linewidth did not exceed 10 GHz. The laser was operated at 500 mW output power across the entire tuning range (2.2 μm-2.81 μm). Overall, the tunability of Cr:ZnSe laser exceeds 1100 nm (between 2000 and 3100 nm) with slope efficiency over 60%. Our experience with microchip SLM Cr:ZnS and ZnSe lasing shows that tens of mW of output power in SLM regime will be readily available in the external cavity laser scheme. Output radiation from this master oscillator will be further boosted up to 500 mW with the Cr:ZnSe power amplifier 14 pumped by Tm fiber laser 22. Measurement, control and absolute calibration of the output wavelength will be performed by monitoring the wavelength of the SLM tunable laser 24 with a Michelson interferometer-based wavemeter 26 (e.g., EXFO, model WA-1500, providing $2 \times 10^{31\ 4}$ nm wavelength accuracy and 1.5-4.0 μm wavelength range).

As mentioned above, OPOs and OPGs are the most promising sources of coherent radiation capable of generating coherent radiation at wavelengths where lasers perform poorly or unavailable. There are several technical approaches to achieve tunable radiation with required narrow spectral line. One approach is based on OPO with intracavity spectral-narrowing elements. The disadvantage of this approach is small tunable spectral range available without mode hoping. Another approach is based on using of injection-seeding OPO configuration. A main limitation of this setup is that the seed wavelengths have to be separated by more than the bandwidth of the parametric gain, and that they have to coincide with resonances of the OPO cavity. As a result, these schemes need an active stabilization of the cavity length.

In contrast to the seeding of an OPO, seeded operation of an OPG is much easier, since the OPG has no optical resonator.

Commercial ps-OPGs and fs-OPGs are now available from several manufacturers, but narrow spectral line OPGs are not available, although the feasibility of these schemes has been demonstrated in the past. Most of the schemes consist of pulsed OPGs excited by SLM pulses of a Q-switched Nd laser system. CW injection seeding radiation of a tunable SLM diode laser narrowed the spectral width of the OPG idler signal. The typical power level of injection seeding laser sufficient to achieve narrow spectral line near 100 MHz was about several mW.

As shown in FIG. 1 to obtain a wide tunability in 2-20 µm spectral range we chose to utilize the OPG-OPA module 20. Basically it is a difference frequency generator (DFG) device where the signal wavelength is injected from the Cr:ZnSe MOPA stage at ~0.5 W level together with a high power pump wave (~1 kW and 10 kHz) from Ho-laser and further amplified in a single- or double-pass through a nonlinear crystal. The main advantages of the proposed OPG-OPA scheme 20 are simplicity of the optical design (no cavity mirrors) and broad tunability, restricted only by phase matching conditions and the crystals optical transparency.

Looking to FIG. 6, an analysis of available Mid-IR nonlinear crystals shows that ZGP, CdSe and GaSe crystals are the best candidates for OPG system operating in mid-IR region. Major optical characteristics of these nonlinear crystals, to be used in the project, in comparison with periodically poled $LiNbO_3$ (PPLN) are further demonstrated in the Table of FIG. 6. Among these crystals ZGP has outstanding fundamental properties as a mid-IR nonlinear crystal. It is especially suitable for high average power applications throughout the infrared region. The large nonlinear coefficient of ZGP, which is approximately 8.8 times that of PLLN, makes it one of the most efficient nonlinear crystals known. Recent improvements in growth of ZGP have led to the ready availability of large (>40 mm), high quality crystals with low absorption in the infrared. Because of some residual absorption below 1.8 µm wavelength, ZGP pump wavelength should be chosen at 2 µm or higher. Thus, 2 µm holmium lasers are good candidates for this purpose. GaSe is also a promising crystal for mid-IR frequency conversion. It has extremely broad transparency range of 0.62-19 µm, and high second order nonlinearity. Unfortunately, GaSe is a layered material, which can be cleaved only along the 001 plane z-cut orientation. On the other hand, due to large birefringence the phase matching polar angles are generally small (11-12°) and a z-cut orientation is quite suitable. CdSe crystal is also promising but has a smallest nonlinear coefficient among ZGP and GaSe.

Figure 7A:
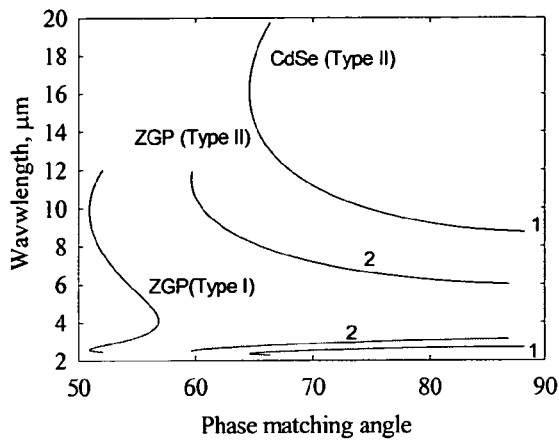
FIGS. 7a-7b are phase matching curves for ZGP type I and II and CdSe type II (FIG. 7a) and GaSe type I interaction (FIG. 7b)
Figure 7B:
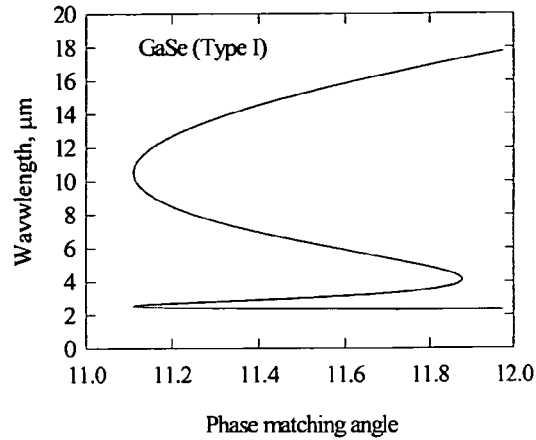

Phase matching curves for signal and idler wavelengths produced by ZGP, CdSe (type I and type II interaction) and GaSe (type I) OPGs for the $\lambda_{pump}$=2.05 µm pump are depicted in FIGS. 7a and 7b, respectively. As it is seen in FIG. 7a, ZGP OPG idler could be tuned over 4.9-12 µm range when seed signal wave is tuned over 3.5-2.47 µm. Utilization of CdSe type II OPG provides idler tuning over 10-20 µm range when seed signal wave is tuned over 2.58-2.28 µm. Alternatively, as shown in FIG. 7b, one can use GaSe type I OPG with idler tunability over 4.9-18 µm when seed signal wave is tuned over 3.5-2.31 µm.

Figure 8:
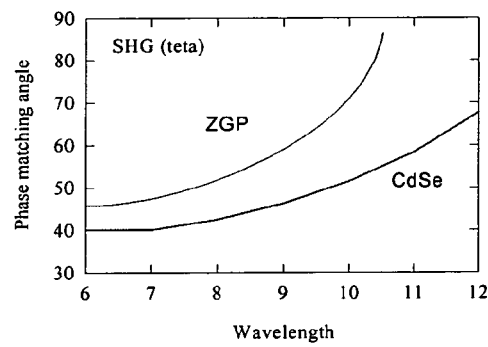
FIG. 8 is a phase matching curve for mid-IR SHG with ZGP and CdSe crystals.
Figure 9:
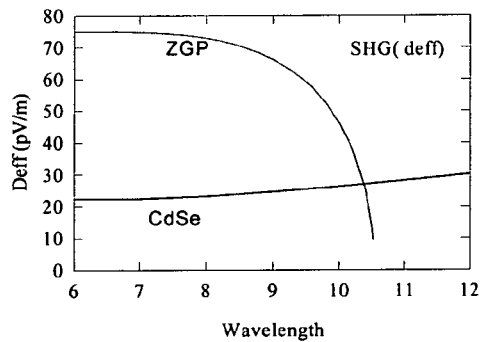
FIG. 9 is a plot diagram of effective nonlinearity vs. SHG process in ZGP and CdSe crystals.

To cover the gap between 3.5 and 5 µm spectral range the second harmonic generation in ZGP or CdSe or $AgGaSe_2$ crystal can be used. Phase matching angle and effective nonlinearity $d_{eff}$ versus idler wavelength for SHG process with ZGP and CdSe crystals are depicted in FIG. 8 and FIG. 9, respectively. One can see that ZGP crystal is a good candidate for SHG in 6-10 µm range. Unfortunately, with increasing wavelengths above 10 µm, the phase-matching angle λ increases up to 90°. This results in reduction in the effective nonlinearity and a lower SHG efficiency. As alternative, CdSe or $AgGaSe_2$ crystals can be used for this application.

Two important conditions should be provided for effective single frequency operation of OPG system. First of all, pump and injected seed lasers should operate in the SLM regime, and, secondly, high gain should be achieved in the nonlinear crystal. SLM operation of the pump and seed laser is already incorporated in our concept. Let us roughly estimate the efficiency of our DFG-OPA system based on utilization of two ZGP 4 cm long crystals, seed power of 0.5 W, and Ho-laser pump power of 10 W at 1 µs pulse duration. To do it, we compare our system with spectrometer developed by Tittel and colleagues. It was based on DFG of 0.65 W and 1083 nm and 1.6 W and 1561 nm radiations (from diode lasers further amplified with Yb and Er/Yb fiber amplifiers) in PPLN crystal. Maximum output power at 3530 nm reached 0.6 mW with efficiency ~0.04%. Taking into account that ZGP FOM is ~9 times larger than one of the PPLN and we use 4 times longer crystal length, the overall efficiency with respect to pump intensity should be more than two orders of magnitude higher (~4%). It translates in the mid-IR power of our DGF-OPA system reaching ~0.5 W. With this level of power (0.5 W comparing to 0.5 mW) and similar detection system our spectrometer should provide much better detection limit for detection of atmospheric formaldehyde than what has been previously reported (0.32 parts per billion in a given volume). Recently successful high efficient ZGP OPO/OPG systems were demonstrated in several publications.

To summarize, the optical nose system works by taking a sampling of molecules into an optical cell. Tunable laser radiation will excite the molecules in the cell, and interaction of light with the molecules gives rise to characteristic absorption spectra. The absorption spectra are fed into a computer-based spectrum recognition algorithm, and molecules are identified and quantified. It is further foreseen that, with respect to the coherent optical detection of molecules, different practical applications of the envisioned optical nose instrumentation 10 require utilization of different trace gas detection methods.

One of the methods is Photoacoustic Spectroscopy (PAS). The laser beam impinges on a selected target gas in a commercially available multipass cell. PAS Light absorption results in a transient temperature rise in the absorbing medium via non-radiative relaxation processes, which then translates into a pressure rise or a sound wave, which is detected with sensitive microphones. One of the advantages of the photoacoustic (PA) technique is that PA detector responsivity is independent of the pump wavelength and linear for a large dynamic range of absorbed power. As a result this technique demonstrates excellent detection sensitivities down to sub-ppbv with powers in the watt range and 0.0006 ppbv for 100 W of pump power. With the present invention we will therefore use photoacoustic detection as the standard reference method as well as for calibration purposes.

A second trace gas technique that will be utilized is multipass cell for long optical pathlength absorption spectroscopy.

A third technique is Cavity Ring Down Spectroscopy (CRDS), which has been shown to be able to trace molecules in the air even with lower power lasers. However, due to the optical resonance intrinsic to the CRDS techniques, its sensitivity depends on the quality of the cavity mirrors, and, hence CRDS cannot be used for measuring review spectra of molecular mixtures in an ultrabroad spectral range. Another problem is a lack of availability of fast detectors operating in the mid-IR. In our design concept we plan to use CRDS mainly for 2-2.4 µm spectral range where InGaAs detectors are still sensitive.

Within the present invention, the detection sensitivity will be further improved with utilization of balanced detection when detected noise will be subtracted from the noise of the probe beam leaving only uncompensated weak absorption signals of interest.

Initially, the wavelength of the present system will be measured by conventional wavelength meters. However, such measurements are usually slow and are not perfect for on-line calibration. For an absolute and relative wavelength calibration of the spectra in the final device, fractions of the mid-IR source radiation will be sent through reference absorbers (gas cells filled with higher concentrations). A relative calibration of the wavelength detuning from reference absorption line is achieved most easily and accurately by monitoring the transmission through one or more Fabri-Perot etalons simultaneously. With the known free-spectral ranges of the etalons and the exact wavelength of a reference absorption line, the absolute wavelength of the Mid-IR source can be determined on-line.

As discussed above, high-energy two-micron holmium lasers are promising candidates for a variety of scientific, medical, and military applications. It has been shown that direct resonant laser pumping of the Ho $^5I_7$ manifold, featuring high cross-section and long (~8 ms) lifetime, results in high energy storage capability and efficient Q-switched operation of holmium laser.

One of the objectives of optical nose technology is to develop a compact single frequency pump laser, e.g. CW Tm-fiber laser pumped, 2.1 μm Q-switched Ho:YAG laser operating at 50 Hz-10 kHz repetition rates with output energy of up to 25 mJ as an effective pumping source of mid-IR (3-12 μm) OPO based on high figure of merit $ZnGeP_2$ (ZGP) crystal. As a compact and cost-effective alternative to the bulk Tm-doped pump lasers, we used a commercially available Tm-fiber laser (Model TLR-30-1908, IPG Photonics Corporation) providing a collimated, diffraction limited beam with the output wavelength of 1908 nm, which corresponds to the strongest absorption line of Ho:YAG.

Figure 4:
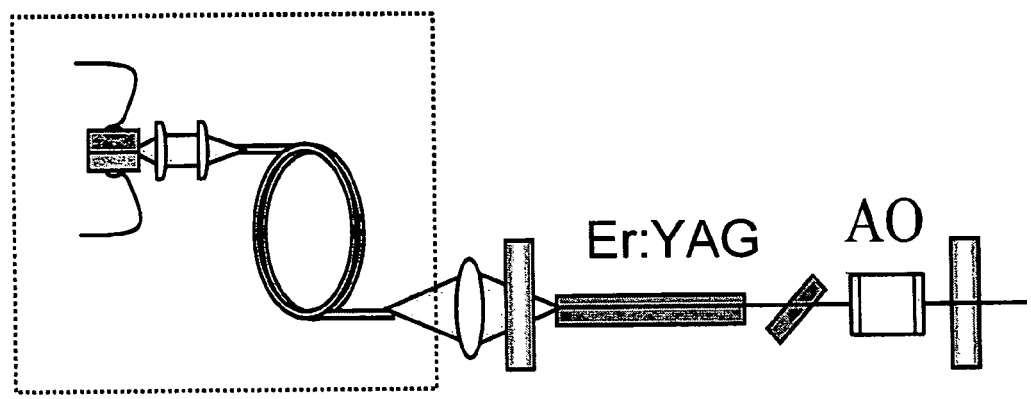
FIG. 4 is a block diagram of the Er-fiber laser pumped Er:YAG laser of the optical nose instrument illustrated in FIG. 2.
Figure 5:
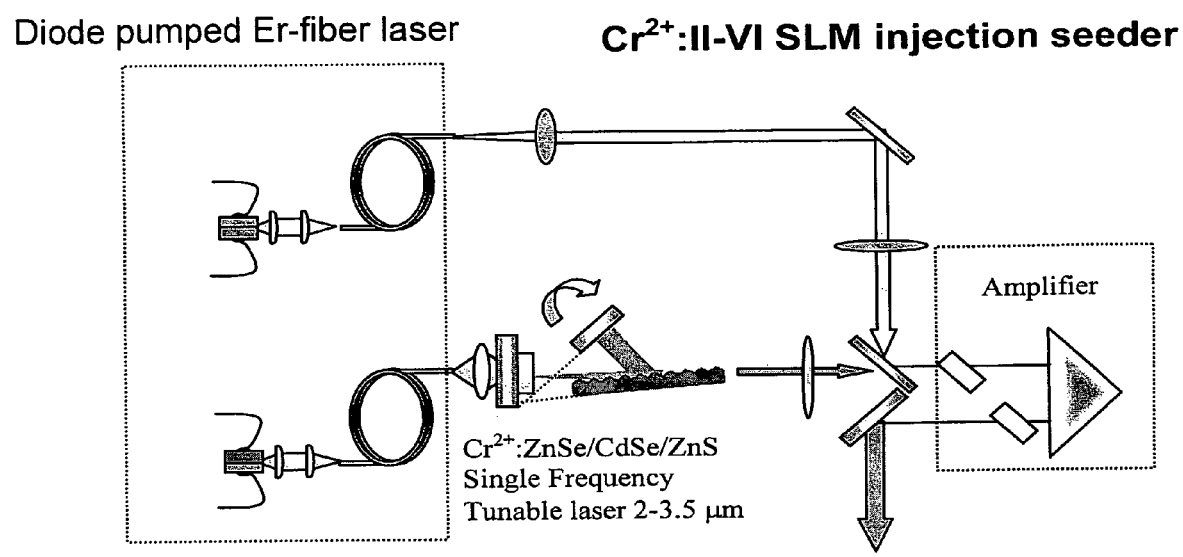
FIG. 5 is a block diagram of the $Cr^{2+}$:II-VI SLM injection seeder of the optical nose instrument illustrated in FIG. 2.

An efficient Q-switched and CW Ho:YAG laser system (2.1 μm) resonantly pumped by a CW 22 W Tm-fiber laser (1.908 μm) was successfully designed at by the inventors (see FIG. 4). In the CW and high repetition rate (10 kHz) Q-switched regimes of operation, the Ho:YAG produces up to 10 W of average output power with a slope efficiency exceeding 50%. At low repetition rates (100 Hz) in Q-switched regime the HO:YAG laser generates high pulse energy of up to 15 mJ with a pulse duration of 17 ns.

Among nonlinear crystals ZGP has outstanding optical, mechanical and thermal properties as well as high laser damage threshold. It is especially suitable for high energy and average power applications throughout the infrared region. The objective of our previous project was the development and characterization of high energy ZGP OPO based laser source operating at 6.45 μm. As a pump source for laser experiments we used the $2^{nd}$ Stokes output of the $Nd^{3+}$:YAG laser shifted to 2.92 μm. The Raman Shifting was realized in $D_2$ Raman cell ($\Delta v=2991$ $cm^{-1}$) pumped by the 1.064 μm radiation of the single frequency Q-switched Nd:YAG laser with a repetition rate of 10 Hz and pulse duration of 7 ns. The maximum output energy of ZGP-OPO exceeded 1.5 mJ at 6.45 μm wavelength with quantum efficiency of 2.92 to 6.45 μm conversion of ~20-22%. Also, we recently demonstrated that the output of tunable 3.9-4.8 μm gain-switched Fe:ZnSe lasers can be parametrically amplified in ZGP OPO system. Thus, Fe:ZnSe laser can serve as a narrow-linewidth single-longitudinal-mode (SLM) seeder for mid-infrared OPO's and OPG's.

Figure 10:
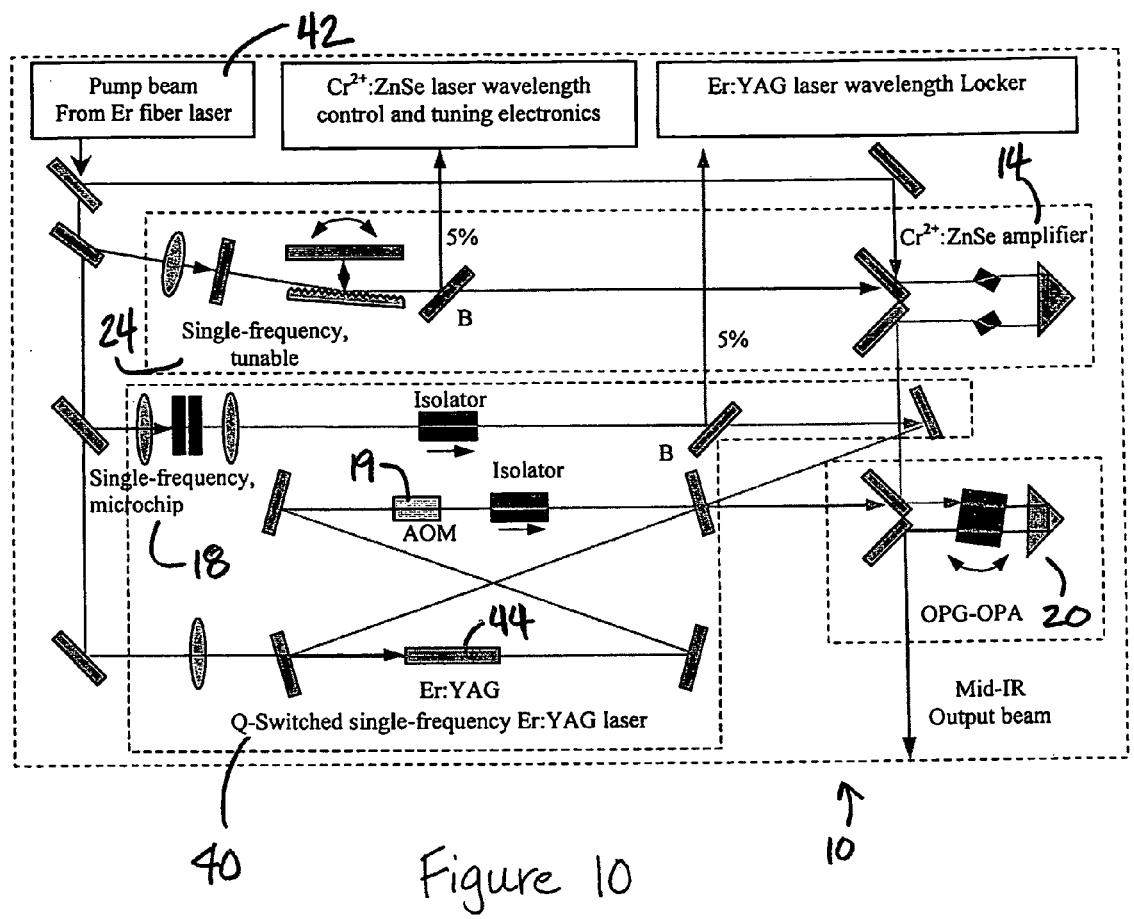
FIG. 10 is a block diagram of the optical nose instrument of the present invention.

Looking to FIG. 10, a modified design has been developed for this operation. In particular, the Q-Switched single frequency Ho:YAG laser 16 is replaced with a repetitively Q-switched Er:YAG (1.65 μm) laser 40, resonantly pumped by a cw Er fiber laser 42 instead cw TM fiber laser 22. This approach of direct laser pumping (using ~1.53 μm) of the $^4I_{13/2}$ manifold featuring long fluorescence lifetime of 13 ms provides access to the high energy storage capability of Er.

The Q-switched Er:YAG laser 40 is used as a pump source for OPG-OPA system 20. In order to achieve wide tuning range of the OPG-OPA system 20 with high spectral resolution, the Er:YAG laser 40 must operate in a single-frequency regime and deliver a narrow and frequency stable laser radiation. Moreover, the Er:YAG laser 40 must deliver high pulse energy of up to 1 mJ at a repetition rate of 10 kHz. To achieve the required characteristics of the pulsed Er:YAG laser 40, the standard approach of locking the Q-switched Er:YAG laser frequency ("host laser") to the frequency of an injection seeding laser is used. The basic idea of this method consists of the process of obtaining a single-mode operation of the pulsed laser by injecting radiation from a narrowband, stabilized, low-power CW laser into the pulsed laser cavity during opening of the Q-switch. Because the intensity of the seeding laser beam is much higher than intensity of spontaneous noise emission of the active material of the host laser system, and the linewidth of the seeding laser is much smaller than the free spectral range of the pulsed laser cavity, the pulse stimulated by the seeding laser will extract most of the energy stored in the host laser active element. This results in a single longitudinal mode of operation of the seeded host Q-switched laser.

The 40 mm-long Er:YAG rod 44 doped with 0.5% of Er and positioned in the ring cavity will be resonantly pumped directly to the $^4I_{13/2}$ manifold by the radiation of the Er-fiber laser. This innovative approach of direct resonant pumping of the solid Er:YAG active medium by Er-fiber laser 42 allows us to fully utilize the excellent energy storage capability of the active material with an unprecedented efficiency. A Brewster-cut acousto-optic modulator 19 is used to Q-switch the Er-laser 42. It is envisioned that similarly to the results of other research groups we will obtain up to 20 W of output power for CW Er-laser, ~10 mJ at 1000 Hz in the Q-switched regime with ~100 ns pulse durations, and ~1 mJ at 10000 Hz with 1-1.5 μs pulse durations. In order to obtain single-frequency operation of the Q-switched Ho:YAG laser 17, a single-longitudinal-mode, low-power (~10 mW), frequency stabilized Er:YAG injection seeding laser, pumped by the same Er-fiber laser, will be used. This will build a single-frequency, Q-switched Er:YAG laser 44 which will produce a diffraction-limited, spatially-stable output laser beam, and generate up to 1 mJ of output energy in 1 μs laser pulses at the repetition rate of 10 kHz.

It is important to note that the following two requirements must be met for the present invention to operate properly for frequency control of the Q-switched laser: (1) the seeding laser must be frequency stabilized and provide a very narrow linewidth; and (2) the pulsed laser cavity optical length must be stabilized against thermal and mechanical fluctuations. In order to satisfy the first condition, a single-mode, low power, stabilized, microchip CW Er:YAG laser 44 will be used as a seeding laser source. Its frequency will be locked to a gas frequency standard using a commercially available precision calibrated laser wavelength locker (e.g. "Wavelength References" LEM-5000), which will provide an absolute wavelength reference. The second issue will be addressed by means of passive temperature and mechanical stabilization of the pulsed laser cavity, and by active control of its length with a piezoelectric (PZT) movable high reflecting mirror of the cavity. The active control of the cavity length is achieved by minimizing the buildup time of the Q-switched laser pulse, which corresponds to the best frequency overlap of the seeding laser line and a longitudinal mode of the pulsed laser cavity. This method has been realized successfully in a number of commercial laser systems (e.g., Spectra Physics pulsed Nd:YAG laser).

The second key component of the optical nose system 10 is the widely tunable $Cr^{2+}$:ZnSe laser 24 used for injection seeding of the OPG 20 must operate in single-mode regime and provide a smooth, mode-hop free wavelength tuning over the entire 2-3.3 μm spectral range. Together with the Q-switched Er:YAG laser pump 40 of OPG 20, this will allow for generation of narrowband IR radiation in the OPG system tunable over 2-10 μm spectral range.

To achieve these goals, the cavity of the $Cr^{2+}$:ZnSe tunable laser 24 must provide a high spectral dispersion and, at the same time, a large spectral bandwidth. The most appropriate dispersion element, which satisfies both of these essential conditions, is a diffraction grating. As noted above, there are two well-studied basic cavity schemes based on a diffraction grating dispersing element: (1) Littman cavity, in which a diffraction grating is mounted at a grazing incident angle, and (2) Littrow cavity, where the diffraction grating is used in the auto-collimation scheme.

Continuous wavelength tuning without any mode hopping can be obtained if the tuning is accomplished by simultaneous controlling of the diffraction grating angular orientation (in the Littrow cavity), or the back mirror reflector (in the Littman resonator), and the resonator length in such a way, that the wavelength feedback scan exactly matches the cavity mode scan. It can be achieved by a proper choice of rotation axis of diffraction grating or the back mirror reflector. This technique was successfully realized in numerous tunable dye and semiconductor lasers used for atomic spectroscopy. A number of semiconductor tunable lasers based on these schemes are commercially available: e.g. the "New Focus Inc" TLB 600 tunable laser offers a continuous tuning over wide (~100 nm) wavelength range around 1550 nm and fast linear sweeps over 100 nm for 2.5 s.

In the present invention, the advantages of these approaches will be combined with extremely broad tunability of $Cr^{2+}$:II-VI lasers in the 2-3.5 μm spectral range. The precise control of the oscillation wavelength in our tunable laser system will be performed by a two-stage controller. During the initial fast scanning, the actual oscillation wavelength will be measured and controlled using a set of Fabry-Perot Etalons. For a slow precision measurements and system calibration a commercially available wavelength meter device (e.g. EXFO WA-1500 Wavemeter), or a precision calibrated laser wavelength locker (e.g. LEM-5000 from "Wavelength References" corporation) will be integrated into our tunable $Cr^{2+}$:II-VI laser system.

This embodiment of the invention includes a single-frequency, widely tunable (over 2-3.5 μm), continuous-wave (CW) laser based on $Cr^{2+}$:II-VI, which will produce a diffraction-limited, spatially-stable output laser beam, and generate up to 0.5 W of output power. Besides the importance for the optical nose system 10, this unique tunable laser system, used as a standalone device, will have a significant impact on many other research fields in the area of high-resolution laser spectroscopy in the mid-IR spectral region.

There are two problems that can occur during realization of the tunable SLM: (1) low output power of the tunable laser, operating in an ultra-narrow linewidth regime, i.e., tens of milliwatts, while the Optical Nose requires up to 0.5 W of the laser output power; and (2) not being able to maintain required continuous ultrabroad (2-3.5 μm) tunability of the laser wavelength without frequency jumps ("mode hopes") in the mid-IR spectral region; in particular, above 2.6 μm the laser will experience additional intracavity losses due to atmospheric water absorption in the cavity, which will lead to "holes" in the laser output spectrum.

To address the first issue, the laser efficiency will be increased, and we may incorporate use of a $Cr^{2+}$:II-VI "master oscillator power amplifier" (MOPA) scheme. The laser efficiency will be increased by applying high quality AR coatings on the surfaces of the $Cr^{2+}$:ZnSe active element and on the intracavity optics; using a more efficient diffraction grating; and increasing concentration and distribution uniformity of $Cr^{2+}$ in the ZnSe host material. Consequent use of a multipass, non-resonator MOPA system will allow for a significant power amplification of the generated single-frequency laser beam.

The second issue of ultrabroad continuous tunability of the laser may be solved by verifying that the mechanical component of the laser system, responsible for angular orientation of the diffraction grating, provides a very precise and stable rotation of the grating around a special fixed pivot point. In addition to a precise rotation of the diffraction grating, the cavity length will be dynamically corrected by fast motion of the laser mirrors with piezoelectric (PZT) transducers; the latter, together with the dynamic monitoring of the generated wavelength, will allow for a precise scanning of the output wavelength with the required accuracy. Finally, to get rid of the intracavity losses due to water absorption, the entire laser housing will be evacuated from ambient air and the laser compartment will be filled with nitrogen; finally, to provide the laser thermal and mechanical stability, its temperature will be stabilized with mK precision by a set of thermoelectric coolers (TEC).

As already mentioned, OPOs and OPGs are the most promising sources of coherent radiation capable of generating coherent radiation at wavelengths where lasers perform poorly or unavailable. There are several technical approaches to achieve tunable radiation with required narrow spectral line. One of them is based on OPO with intracavity spectral-narrowing elements. Using this approach, the single-frequency oscillation in the mid-IR spectral region has been demonstrated. The disadvantage of this approach is a small tunable spectral range available without mode hoping. Another approach is based on using of injection-seeding OPO configuration. A main limitation of this setup is that the seed wavelengths have to be separated by more than the bandwidth of the parametric gain, and that they have to coincide with resonances of the OPO cavity, which requires an active stabilization of the cavity length.

To obtain a wide tunability in 2-10 μm spectral range we chose to utilize the OPG-OPA concept. Basically it is a difference frequency generator (DFG) device where the signal wavelength is injected from the Cr:ZnSe MOPA stage at ~0.5 W level together with a high power pump wave (~1 kW & 1-10 kHz) from Er-laser and further amplified in a single- or double-pass through a nonlinear crystal. The main advantages of the proposed OPG-OPA scheme are simplicity of the optical design (no cavity mirrors) and broad tunability, restricted only by phase matching conditions and the crystals optical transparency.

Figure 11:
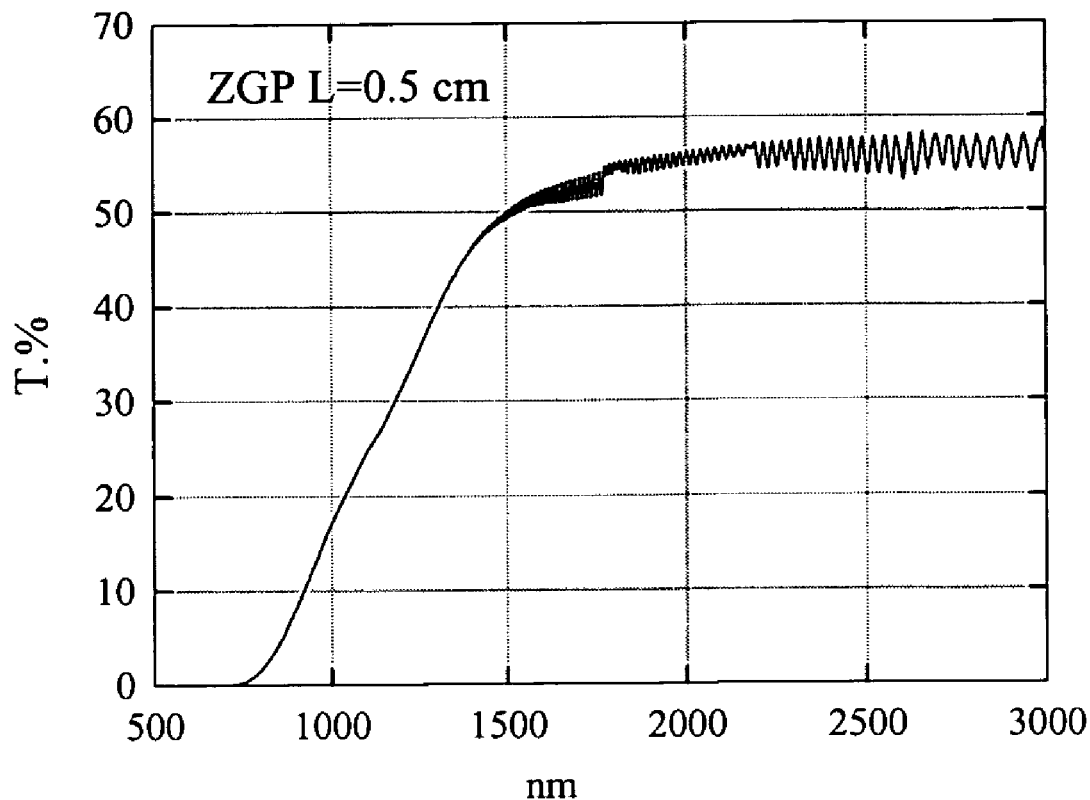
FIG. 11 is a transmission spectrum of ZGP crystal over 500-3000 nm spectral range. It shows that current technology of after growth crystals treatment allows decreasing residual absorption of the ZGP crystal at wavelength >1.6 μm and utilization of Er:YAG laser (1.65 μm) as a pump source for ZGP based OPG.

Analysis of available mid-IR nonlinear crystals shows that ZGP crystal is one of the best candidates for OPG system operating in the mid-IR region. It is especially suitable for high average power applications throughout the infrared region. The large nonlinear coefficient of ZGP, which is approximately 8.8 times that of periodically poled lithium niobate (PLLN), makes it one of the most efficient nonlinear crystals known. Recent improvements in growth of ZGP have led to the availability of large (>40 mm), high quality crystals with low absorption in the infrared. As demonstrated in FIG. 11, current technology of after growth crystals treatment allows decreasing residual absorption of the ZGP crystal at wavelength >1.6 μm. As a result the Q-switched Er-YAG can be used as a pump source of ZGP-OPG system. This laser source operating near 1.65 μm together with seeding radiation of tunable $Cr^{2+}$ laser in 2-3.3 μm can provide a simple laser system tunable over 2-10 μm spectral range.

Figure 12:
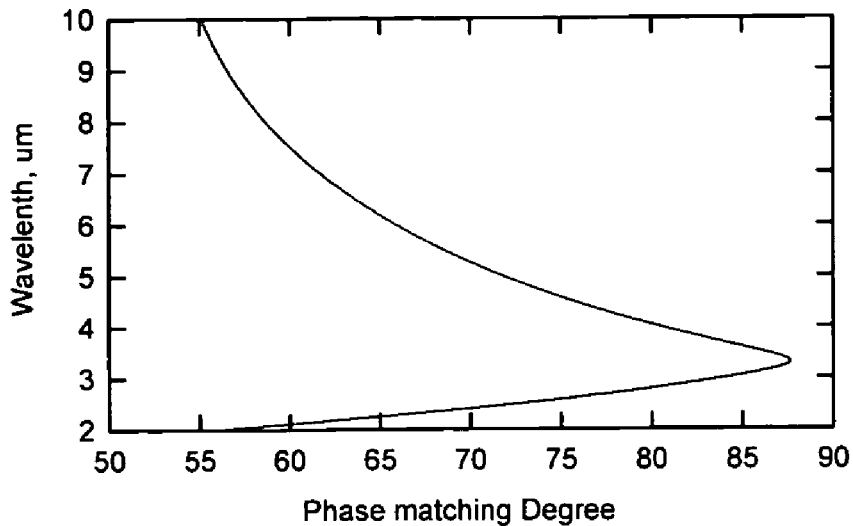
FIG. 12 is a phase matching curve for signal and idler wavelengths produced by ZGP, (type I interaction) OPG for the wavelength (pump) at 1.65 μm at y=390 K.

Phase matching curves for signal and idler wavelengths produced by ZGP OPGs for the $\lambda_{pump}$=1.65 μm pump are depicted in FIG. 12. As it is seen in FIG. 12, ZGP OPG idler could be tuned over 3.3-10 μm range when seed signal wave is tuned over 3.3-2.0 μm. Two important conditions should be provided for effective single frequency operation of OPG system. Firstly, pump and injected seed lasers should operate in SLM regime; secondly, high gain should be achieved in the nonlinear crystal. SLM operation of the pump and seed laser is already incorporated in our concept.

A single-pass power parametric gain factor (for zero phase mismatch) is expressed as $$G = P_{in}/P_{out} = \cosh^2(\Gamma L),$$

where L is the length of the nonlinear crystal and Γ is the gain increment given by:

$$\Gamma^2 = \left(\frac{d_{eff}^2}{n_1 n_2 n_3}\right) \frac{8\pi^2 I_{pump}}{\lambda_1 \lambda_2 \varepsilon_0 c},$$

where $I_{pump}$ is the pump laser intensity (power density)[W/$m^2$], $\lambda_1$ and $\lambda_2$ are idler and signal wavelengths [m], $d_{eff}$[m/V] is the effective nonlinearity, $n_i$ is the average refractive index, $c=3\times10^8$ [m/s] and $\varepsilon_0=8.854\times10^{-12}$ [As/Vm]. The first term is also referred as the nonlinear optical figure of merit (FOM) of the crystal. To achieve a threshold of a single-pass OPG, one needs G ≈$10^{10}$, corresponding to ΓL≈12. Let us roughly estimate the efficiency of our OPG system based on utilization of double pass in 2 cm long ZGP crystals, pumped by 1 mJ Er-laser pulses focused in 150 μm spot with 100 ns pulse duration. The nonlinear gain calculated using these parameters of the pump radiation is equal to be ΓL=12.6. Crystal angular tolerance for these interactions is several mrad and can be controlled with commercial available rotational stages. Also required temperature stabilization of the nonlinear crystal can be easy provided.

One of the important elements of the present invention is the design and optimization of the optical scheme of the OPG unit. Optical design should provide focusing and spatial overlapping of the pumping and seeding beams in the nonlinear crystal, optimization of the numbers of round trips in the nonlinear crystals; and spectral separation of signal and idler radiation at output channel. Special consideration will be implemented to choose and stabilize operating temperature of the nonlinear crystal. This parameter determinates phase matching angle, nonlinear conversion efficiency, and optical damage threshold of the nonlinear crystal. Therefore optimization of the operation temperature will be essential part of the unit design.

For this embodiment, a narrowline, pulsed OPG system is built, tunable in the real time over 2-10 μm wavelength range, which will provide us with the capability of fast spectral analysis of biomarker molecules contained in the exhaled patient breath. Optical parametric oscillators and generators based on the ZGP crystal are well known. However, as one can see from the FIG. 12, to provide tunability over 2-10 μm the angular tuning of the ZGP crystal should span over a large 56-85° range of angles. This big range of phase-matching angles could be difficult to realize in one nonlinear ZGP crystal. Also, for the phase matching angles near 90° the efficiency of the nonlinear frequency conversion in ZGP crystal will decrease. One way to solve the problems is to increase temperature of the ZGP crystal that will lead to smaller span of phase matched angles and shift them further from 90°. Another way is to use additional nonlinear crystal for OPG in 3.3-4.5 μm spectral range. First, it will decrease the range of tuning angle of ZGP crystal and result in a better optimization of nonlinear conversion efficiency. Second, it will increase the conversion efficiency in 3.3-4.5 μm spectral range where ZGP might have small nonlinearity. One of the best candidates for the second nonlinear crystal for the 3.3-4.5 μm spectral range is $AgGaSe_2$ nonlinear crystal which features even higher nonlinearity than ZGP crystal in this spectral range for 1.65 μm excitation.

As mentioned above, different practical applications of the envisioned optical nose instrumentation require utilization of different trace gas detection methods. The main detection technique that will be used in this embodiment is Photoacoustic Spectroscopy (PAS). The major advantage of the PAS technique is that its detection responsivity is completely independent of the pump wavelength and is linear for a large dynamic range of absorbed power. As a result, this technique demonstrates excellent detection sensitivities down to sub-ppbv with powers in the watt range and 0.0006 ppbv for 100 W of pump power. The second advantage of PAS technique is the ability to detect minute concentrations of absorbing molecules in a presence of other components at the atmospheric pressure. Thus, PAS method requires minimal or no sample preparation and can be carried out in real time, constantly monitoring patient status.

Although the basic idea of the PAS method is known, it could not be used to its full extent until appearance of lasers. PAS has one of the highest sensitivity among gas tracing methods and is being widely used recently for air pollution monitoring and detection of volatile organics components. Nevertheless, this technique is yet to become versatile due to lack of available tunable lasers in the middle- and the far-IR spectral regions.

Figure 13:
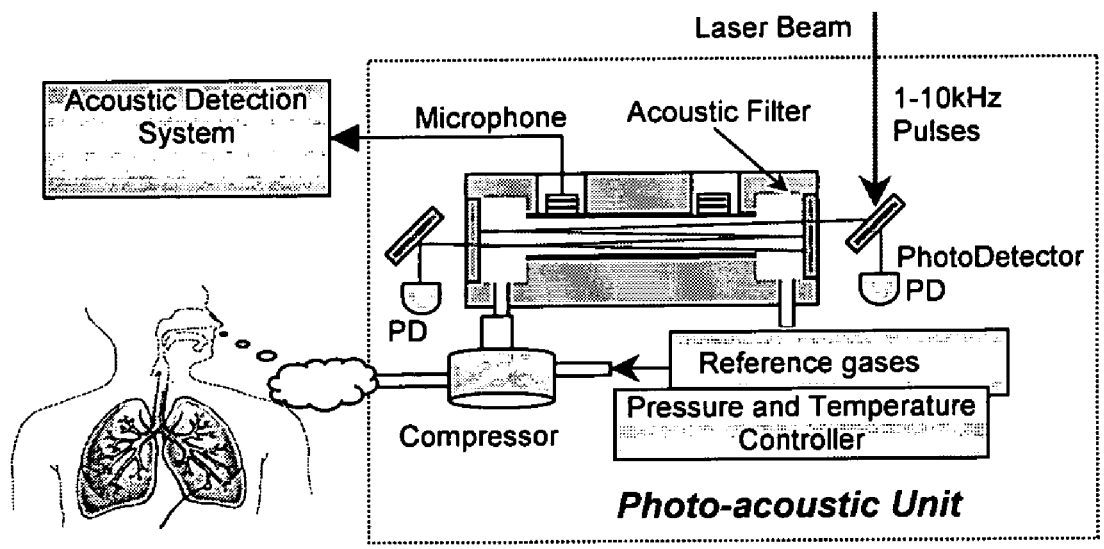
FIG. 13 is a schematic diagram of a photoacoustic detector.

The principle of PAS is depicted in FIG. 13. The pulsed, tunable laser beam passes through the test cell and is absorbed by the gas molecules when the laser wavelength corresponds to the molecules' absorption lines. A significant part of the absorbed laser light energy is transferred almost instantly to the thermal energy of the gas molecules, increasing local temperature and pressure. When the repetition rate of the pulsed laser beam is smaller than the reciprocal thermal relaxation time, a sound wave (periodic pressure variations) is formed. This sound wave can easily be detected by a sensitive microphone placed inside the cell, indicating the laser light absorption. The intensity of the sound wave is a function of the total absorbed light energy and, therefore, it serves as a measure of the absorbing molecule concentration in the cell. The Optical Nose laser wavelength will continuously be tuned over the 2-10 μm fingerprint spectral region, and the device will pinpoint all absorption bands of the molecules of the multicomponent gas mixture in the test cell. The sensitivity of this method will further be significantly increased (by two orders of magnitude or more) by using a multipass absorption cell. A very sensitive and fast PAS detector for precise measurements of absorption lines of the fingerprints spectra of the pathogen organic molecules in the spectral region of 2-10 μm.

A potential problem with this embodiment is that the pulsed laser light will also be absorbed by the reflecting windows of the test cell producing a background sound noise, which will affect the detection sensitivity. The solution to this problem involves using the cell material with the minimum absorption in the operating spectral region of 2-10 μm. The detection sensitivity will further be improved, and the background noise significantly reduced, by means of utilization of balanced detection technique with a lock-in amplifier. This method will allow for subtraction of the detected noise signal from the useful sound signal, leaving only uncompensated weak absorption signals of interest.

Figure 14:
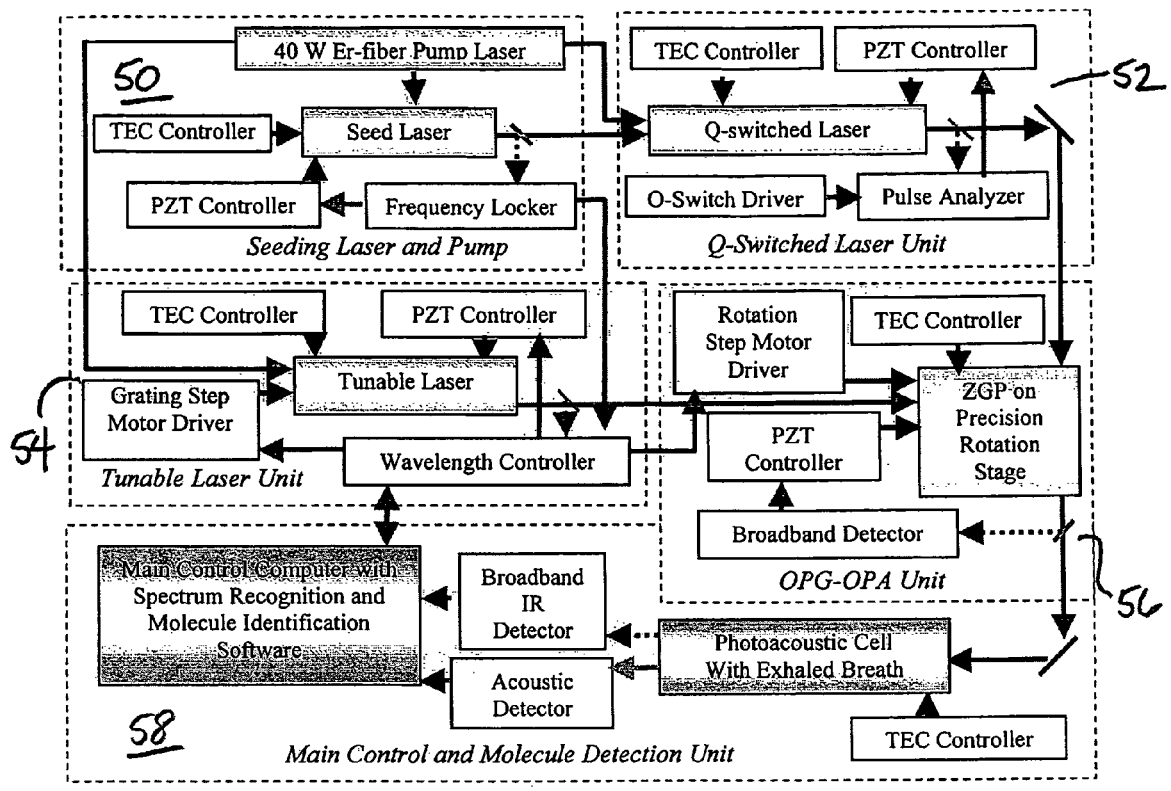
FIG. 14 is a control flow and block diagram of the optical nose system.

Referring now to FIG. 14, an overall block diagram and control flow chart of the optical nose system 10 is illustrated. From the control and packaging point of view, the Optical Nose system includes five major units: (1) seeding and pump lasers unit 50; (2) Q-switched OPG-pump laser unit 52; (3) tunable laser unit 54; (4) OPG-OPA system unit 56; and (5) main control and molecule detection unit 58. Operation of the system 10 begins with the seeding laser serving as the main wavelength reference device. It includes a continuous wave (CW) microchip, single-frequency Er:YAG laser and an absolute frequency standard ("Laser Frequency Locker"). The absolute frequency standard is based on a gas cell with narrow absorption spectral lines in the 1500-1700 nm spectral region, and an electronic control block that provides feedback to the single-mode laser mirrors. By continuously monitoring the single-mode laser wavelength, the frequency locker locks it to one of the absorption lines of the gas cell. This way the seeding laser frequency can be stabilized at a certain value with an extremely high accuracy. The laser cavity will be made of a low thermal expansion material and kept at a constant temperature with an accuracy of $10^{-3}$ K for reliable frequency stabilization.

The Q-switched Er:YAG laser, operating at 10 kHz repetition rate, serves as the pump source for OPG-OPA generator. It must provide narrow-linewidth, single frequency, stable, pulsed laser radiation for reliable operation of the OPG. For this reason, its lasing frequency is locked to the master frequency of the seeding laser. The injected laser light forces the pulsed laser to operate at the exact wavelength of the seeding laser.

However, mechanical and thermal oscillations may cause some wavelength mismatch between the seeding laser and the pulsed laser. To achieve a reliable locking of the Q-switch laser wavelength to that of the seeding laser, the cavity length of the Q-switched laser will be actively stabilized by two methods: (1) the long term coarse stability is achieved by proper mechanical and thermal stabilization of the laser cavity; (2) one of the pulsed laser cavity mirrors is mounted on a PZT, and the laser cavity length is controlled by constantly monitoring the buildup time of the generated laser pulses: minimum pulse buildup time corresponds to the optimum overlap between the seeding, and pulsed laser spectral lines.

The CW $Cr^{2+}$:II-VI widely tunable laser is the second major laser source for operation of the OPO system and generation of the laser radiation in the 2-10 μm spectral range. It must provide a narrowband laser radiation, continuously tunable in the spectral range of 2-3.5 μm without any frequency jumps ("mode hopes"). As described earlier, this widely tunable laser will be based on the Littrow or the Littman laser scheme. In both those schemes, it is extremely important to rotate the diffraction grating (Littrow) or the back reflector mirror (Littman) around a certain pivot point with very high accuracy. The pivot point must be fixed with a tolerance of several micrometers and the rotation of the grating (or the mirror) must be performed with an accuracy of $10^{-3}$ radians. In order to achieve such precision, the laser housing will be thermally and mechanically stabilized. Small and fast corrections of the generated laser wavelength will be additionally performed by changing the laser cavity length by means of longitudinal displacements of one of the laser mirrors with a PZT. The wavelength controller receives three signals: (1) the commands from the main computer, which tells it so sweep the laser over a certain wavelength range; (2) the feedback signal from its internal wavemeter, which constantly monitors the tunable laser wavelength; and (3) the signal from the seeding laser frequency locker, which serves as an absolute wavelength reference for the tunable laser. It then calculates the required rotation angle of the diffraction grating for obtaining the desired wavelengths and sends appropriate commands to the grating stepping motor controller for a coarse wavelength sweep, and to the PZT controller for precision wavelength corrections. As a result, the laser generates the light with the desired wavelengths with a high precision.

The OPG-OPA is based on a single ZGP nonlinear crystal generated radiation over the 2-10 μm mid-IR spectral range. It is extremely important to set the angular orientation of the ZGP crystal according to the laser wavelength incoming from the $Cr^{2+}$:II-VI tunable laser. Consequently, the ZGP crystal must be rotated synchronously with changing the wavelength of the tunable laser. For this reason, the controller of the ZGP stepping motor rotation stage constantly receives the information about the current wavelength from the wavelength controller of the tunable laser. It then calculates the required angle of rotation of the ZGP for the current wavelength and rotates it accordingly. In addition, an independent PZT serves for a fine tuning of the ZGP angular orientation. That is, the PZT controller receives a signal form a broadband detector and fine-tunes the ZGP angular orientation until the signal is maximum. As all the other laser units, the ZGP crystal is thermally stabilized (possibly at a temperature of about 400°K).

The major component of the detection unit is the absorption gas test cell which contains the gas sample to be analyzed, such as the patient's exhaled breath. PAS is a very sensitive and fast method for measuring the absorption spectra with very high sensitivity, independently of the incident wavelength. The acoustic signal from the cell's built-in sensitive microphones, operating at the frequency equal to the repetition rate of the Q-switched laser, is sent to the main computer, which receives the information about the current wavelength from the tunable laser wavelength controller. The computer then calculates the current wavelength incident into the test cell and records the dependence of the signal from the acoustic detector versus the incident laser wavelength. The computer controller then performs a complex analysis of the measured absorption spectrum by comparing it to the known absorption spectra of the gases of interest. As a result, the software algorithm will identify the organic components contained in the patient breath. The data acquisition and control system will monitor the device components and generate control signals based on programmed feedback algorithms. Algorithm development for comparison of real time signals with characteristic absorption spectra and identification of specific recognized patterns will rely on classical least-squares (CLS) and nonlinear least-squares (NLS) fittings.

In one embodiment, the optical nose system 10 will be packaged in a standard 19" rack configuration to minimize its footprint and to allow for easy transportation. The optical platforms may be fabricated from Kovar or a similar low coefficient of expansion material, and will be rigidly interconnected to maintain optical alignment. The rigid optical subassembly will be isolated from the rest of the rack to reduce vibration from cooling fans or from room vibrations. The optical system enclosure will be thermally regulated to further reduce tuning drift. The laser source unit, as well as the Er fiber pump laser, will be enclosed in 4U 19" rack mount blocks. The Michelson interferometer-based wavemeter has dimensions of approximately 20 cm×29 cm×30 cm (W, D, H), which also fits into this Rack mount chassis. Another such block with the same dimensions will be used for a laser controller unit, which will contain the following modules: 1) electronics for the temperature stabilization of the laser unit, 2) the locking electronics for the frequency stabilization of the single-frequency Er:YAG seeding laser, 3) the controller for the AOM of the Q-switched Er:YAG laser, and 4) the controller of the single-mode tunable $Cr^{2+}$:ZnSe master oscillator.

The overall control of the electronic modules and their interactions will be performed from a compact central computer that will also be mounted in a separate 4U 19" rack mount block. All five blocks will be integrated into a single movable box with dimensions of approximately 50 cm×64 cm×100 cm (W, D, H).

Figure 15:
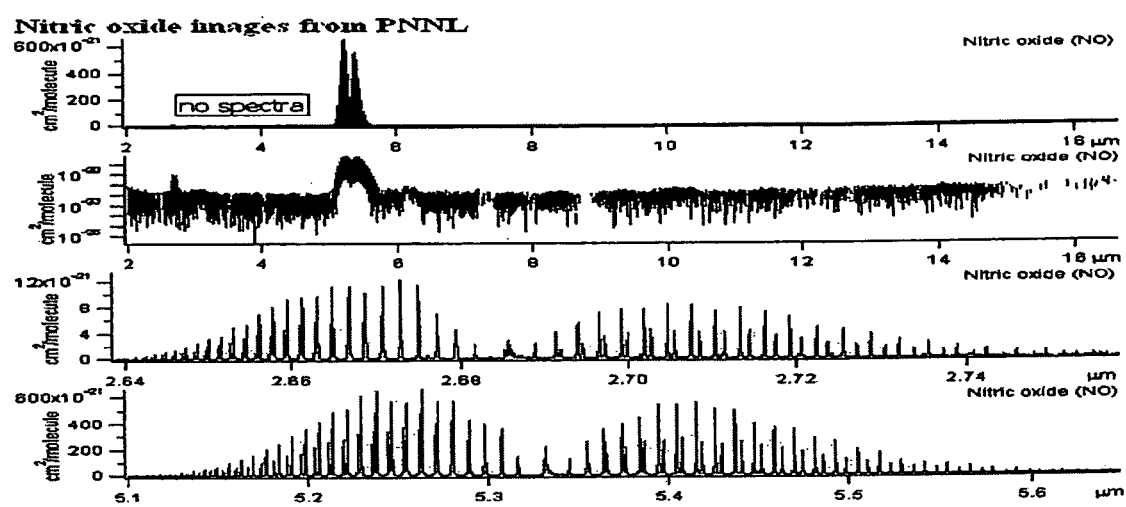
FIG. 15 is an example of spectroscopic fingerprint (absorption spectrum) of nitric oxide.

The present invention can be used in a variety of applications. Applications of the optical instrument will be counter-terrorism related applications such as the detection of explosives, chemical and biological warfare agents and their precursors, industrial process control, and biomedical applications, i.e. detecting biomarkers associated with malignant tissues and measurement of medically important molecular compounds in the exhaled breath of patients. For example, FIG. 15 shows the spectroscopic fingerprint of nitric oxide, which is a biomarker for lung cancer, asthma, and diffuse anbronchiolitis. Other biomarkers could be found for carbon monoxide (cystic fibrosis or diabetes); ethane (cystic fibrosis or body ionizing irradiation); pentane (myocardial infarction); isoprene, hexane, butane, methane, or formaldehyde (lung cancer); hydrogen peroxide (asthma or bronchiectasis); ammonia, pyrozines, or cyclohexanone (diabetes); or $^{13}C$ (gastric ulceration or chronic gastritis).

The laser optical nose instrument will operate over the spectral range of molecular fingerprint region (2-20 μm) to provide direct access to the strongest absorption lines of environmentally, chemically, biologically, and medically relevant trace gas molecules and is expected to have a broad technological relevance for many different fields of science and technology.

It is foreseen that the present invention will have a wide variety of applications. One such application is in the analysis of breath constituents as a way of early diagnostics or monitoring of human health. Breath may contain useful markers of many diseases. In 1971, Pauling and co-workers reported that normal human breath contains a complex mixture of several hundred volatile organic compounds (VOCs). Since most VOCs are exhaled in picomolar concentrations, the proposed optical nose is ideal candidate for VOCs detection. Breath testing will save time, and will be much cheaper and patient friendly than existing procedures, making it socially and economically relevant technique. Moreover, full chemical specificity, ultimate sensitivity, and highest (real time) speed of the optical nose grants it a potential to become a powerful tool for monitoring physiological and pathological processes in the whole body. Several specific examples are illustrated below.

It was additionally been found that the ethane concentration in breath correlates with the radiation dose received and also with acute nausea and vomiting experienced by patients undergoing radiation therapy. It is believed that the breath ethane generation during total body irradiation is a marker of radical mediated lipid peroxidation. It is also believed that monitoring of ethane concentration in breath during radiation therapy could help determine and follow the optimal irradiation protocol, in order to maximize the effect on the cancer cells, while keeping the risk of other complications minimal.

S. Kharitonov and P. Barnes demonstrated evidence that breath analysis will play an important place in the diagnosis and management of lung diseases in future. Many lung diseases, including asthma, chronic obstructive pulmonary disease, cystic fibrosis, and interstitial lung disease involve chronic inflammation and oxidative stress. Unfortunately, at the moment single exhaled markers are usually evaluated in isolation, markers are affected differently in different diseases and different markers vary in their sensitivity to certain maneuvers such as the effect of therapy. For example, asthma is characterized by a large increase in exhaled NO (30-40 ppb), a modest increase in CO, and a modest increase in exhaled 8-isoprostane. By contrast, patients with cystic fibrosis typically have low exhaled NO concentrations and high levels of exhaled CO and 8-isoprostane.

Recently, attention has focused on the use of molecular methods to detect tumor markers in clinical samples from lung cancer patients. These include the identification of abnormal cytomorphology and genetic mutations in cells from sputum and bronchoalveolar lavage (BAL) fluid which require lengthy and complicated processing and analysis. Other studies have identified protein biomarkers in BAL fluid which can discriminate between lung cancer patients and controls. Bronchoscopy and sputum induction are lengthy and expensive procedures which are not suitable for routine clinical use and are not risk-free. In recent years the analysis of exhaled breath for the diagnosis and monitoring of lung diseases has gained increasing attention due to its non-invasive nature and ease of use. More than 3,000 volatile organic compounds have been detected in exhaled breath and most of these are present in picomolar concentrations which are below the detection limit of most current sensors.

Biomarkers of lung disease have been measured directly from breath in the gaseous phase, such as nitric oxide, and in water condensed from exhaled air (exhaled breath condensate or EBC). Many organic molecules have been identified from EBC, including proteins such as cytokines and growth factors, making it a feasible approach for the detection of biomarkers in lung cancer. Methodological issues exist with the use of EBC, including standardization, dilution and reproducibility. However, recommendations for the use of EBC have recently been published by the American Thoracic Society and EBC will continue to evolve as a powerful non-invasive tool for the investigation of lung diseases in human patients. Several studies have explored the use of exhaled breath in the diagnosis of lung cancer using subjects with diagnosed lung cancer awaiting surgery. These studies analyzed a small number of volatile organic compounds in the gaseous phase using gas chromatography and mass spectrometry. Analysis was mostly qualitative and not quantitative and performed at a separate time from collection. However analysis of volatile organic compounds discriminated lung cancer patients from controls with reasonable sensitivity and specificity in these studies, indicating the potential of this approach. A device such as the "optical nose", which is capable of detecting all organic compounds present in exhaled breath on-line with extreme sensitivity and specificity, could greatly improve the performance of current screening techniques. Such technology would be capable of quantifying a large number of known and novel biomarkers for lung cancer, thereby creating specific recognition patterns or "fingerprints" for the disease. This would revolutionize the care of lung cancer patients with vast improvements in cure rates, decreased morbidity and increased survival.

In addition to the embodiment for detecting the first signs of lung cancer, the present invention may also be used in revealing and characterization of the behavior of combination of new biomarkers—diagnostic fingerprints of different pulmonary diseases. A special attention will be addressed to studies of characteristic effects of therapeutic treatments on these markers since this may improve the specificity of treatment in the future. It might even be possible, in future, to identify a specific pathogen, hence to apply the most appropriate antibiotic therapy by studying the patients' hydrocarbon profile. Furthermore, the present invention may be used to determine exhale breath profile of different hydrocarbons for a variety of clinical condition making an emphasis on "sniffing out" the lung cancer in its early stages.

Hydrocarbons are markers of lipid peroxidation, which is one of the consequences of the constant and inevitable formation of oxygen radicals in the body. During the process of peroxidation of polyunsaturated fatty acids hydrocarbons are distributed in the body, partly metabolized, and exerted in the breath, making it possible to estimate the magnitude of in vivo lipid peroxidation. Laser optical nose instrumentation will be used for development of database of exhaled breath profiles of hydrocarbons related to different diseases, which is much more informative than information on single hydrocarbons.

The present invention may also be used in the monitoring of lipid peroxidation of astronauts as early diagnostics of possible pathological processes during long-term space flights simulations as well as during envisioned flights to the Moon and Mars. It is noteworthy that first attempts of monitoring single hydrocarbons in cosmonauts during long-term space flights have been recently reported by Poliakov et al.

For nutrition and health studies dietary food and food additives are often labeled with stable isotopes such as $^{13}C$. Consequently, the optical nose instrumentation may be used for detection of metabolites derived from such labeled food additives. Thus, from these few examples (among numerous potential options), one can see that the development of novel optical nose instrumentation will have a huge impact on biomedical research on understanding life processes, early diagnosis, prevention, and treatment methods.

Prospecting for oil and gas is usually an expensive and time consuming process, involving bouncing sound waves through rock layers to see if they might be capable of trapping hydrocarbons. Results can take several months to interpret and even then there is no guarantee that the rocks do contain oil. At the same time oil and gas reservoirs naturally leak tiny traces of hydrocarbons such as ethane (ppb level) into the atmosphere. It is believed that optical nose instrumentation will provide much cheaper, quicker, and more reliable method than traditional techniques of revealing whether oil and gas are actually present. To prospect for oil and gas measurements of ethane and wind direction will be combined to locate the likely sources.

The present instrumentation may also be utilized for monitoring hazardous wastes relevant to national and local needs, such as: 1) Sensing of pollution and chemical warfare agents; 2) Monitoring of hazardous waste and munitions disposal; 3) Species-specific gas monitoring in production facilities 4) Tracking of naturally occurring gas emitters—methane seeps and volcanoes, as well as 4) Stand-off assessment of explosion hazards such as fuel leaks.

The exchange rate of gaseous species between the earth, oceans, and the atmosphere is a major factor determining the composition of the atmosphere. These processes are difficult to model in the laboratory and should be studied in situ. We envision that laser optical nose instrumentation will be utilized by researchers investigating atmospheric trace compounds relevant to climate studies. These studies could provide valuable information on global climate changes leading to better understanding of dynamics of the earth atmosphere and more accurate weather forecasting.

Trinitrotoluene (TNT) is the most commonly used explosive for terrorist devices and is a component of most military-grade devices. Dinitrotoluene (DNT) is formed during the manufacture of TNT and is present in small quantities in most TNT, as well as smokeless and black powders. It is not uncommon for the concentration of DNT to be higher than that of TNT in the vapor samples collected near explosive devices. This is because the vapor pressure of DNT is greater than that of TNT. Most military grade explosives contain TNT and DNT. Even ammonium nitrate explosives usually contain DNT and TNT. The laser optical nose is capable to detect volatile components of TNT, DNT, and ammonium nitrate with ultimate sensitivity, and real time speed.

Envisioned high-power, broadly tunable, and versatile mid-IR laser and its prototypes would impact military applications such as aircraft-, and ship, and satellite-based countermeasures, remote sensing for chemical warfare detection and counter-proliferation intelligence gathering. In addition, the source could find application in advanced laser-based, eyesafe seekers for smart munitions and cruise missiles and in covert communications systems. The proposed laser system is ideal for countermeasures. Its output wavelengths would encompass all countermeasure bands, and thus be suited for use against all known seekers. Also, the wavelengths generated would fall in the 3-5 μm and 8-11 μm regions of atmospheric transmission suited for chemical vapor detection, with applications to counter-proliferation and chemical agent detection. Such sensors would also be invaluable in the search for weapons of mass destruction.

While our invention has been disclosed in various forms, this disclosure is not to be construed as limiting the invention solely to these forms; rather the invention is limited solely by the breadth of the claims appended hereto.

What is claimed is:

1. An optical nose system having a broadly tunable, narrow linewidth mid-IR laser source wherein the laser source has a modular structure and comprises
   a) a tunable seed laser unit including a single-longitudinal mode, widely tunable $TM^{2+}$:II-VI master oscillator with a $TM^{2+}$:II-VI power amplifier having a laser output, where $TM^{2+}$ stands for transition metal ion selected from the group consisting of $Cr^{2+}$, $Fe^{2+}$, $Co^{2+}$ and $Ni^{2+}$, and II-VI stands for ZnS, ZnSe, CdS, CdSe, ZnTe, CdTe and their mixtures wherein said seed laser is a broadly tunable single frequency laser without mode hoping which is comprised of Littrow or Littman dispersive cavity with accompanied by dynamic correction of cavity length;
   b) a pulsed pump laser unit including a single-frequency, high energy, Q-switch laser having a laser output;
   c) an Optical Parametric Generator-Amplifier, pumped by said pulsed pump laser unit and seeded by said seed tunable laser unit having a mid-IR output selectively variable over about 2 to 20 μm; and
   wherein said pulsed pump and seed tunable lasers are pumped by a single diode, diode array, or fiber laser.

2. The optical nose system as defined in claim 1 wherein correction of cavity length is controlled by piezoelectric transducers.

3. The optical nose system as defined in claim 2 further comprising a Master Control Computer, single frequency pump pulsed laser unit with a wavelength locking, single frequency seed tunable laser unit with a feedback system for frequency stabilization, Optical Parametric Generator-Amplifier and wherein the length of said seed tunable laser cavity is controlled by a piezoelectric controller, a grating step motor driver connected to a step motor for diffraction grating or mirror of the tunable laser cavity, a wavelength controller operatively connected to send signals to said grating stepper motor driver dependant on inputs from said master control computer.

4. The optical nose system as defined in claim 3 wherein said Optical Parametric Generator-Amplifier is a difference frequency generator device where the laser radiations from the seed tunable laser unit and a high power pump laser unit are mixed in nonlinear crystal, selected from the group of ZGP, CdSe or GaSe.

5. The optical nose system as defined in claim 4 wherein the orientation of said nonlinear crystal is controlled by a rotation step motor receiving a control signal from said wavelength controller.

6. A method for analyzing a gaseous sample contained in a photoacoustic gas cell, said method comprising the steps of:
   a) pumping a pulsed pump and tunable seed lasers and generating laser oscillation of the said lasers;
   b) pumping optical parametric generator-optical parametric amplifier unit (OPG-OPA) with radiations of the pulsed pump and seed lasers and generating of tunable mid-IR signal and idler waves;
   c) directing a tunable laser radiation from said OPG-OPA to the gas cell and measuring absorption spectrum; and
   d) comparing the measured absorption spectrum with the known absorption spectra of the gaseous sample to determine the composition of the gaseous sample;
   wherein
      step a) further comprises: Pumping of the said seed and pulsed pump lasers with Tm-fiber or Er-fiber pump lasers, and
      step b) further comprises the step of
         providing a ZGP nonlinear crystal in said OPG-OPA generating radiation over the 2-10 µm mid-IR spectral range,
         rotating the position of said ZGP nonlinear crystal with a ZGP stepping motor,
         providing a wavelength controller connected with a ZGP stepping motor,
         calculating the required angle of rotation of the ZGP for the current wavelength, and
         rotating the ZGP according to calculations.

7. A method for analyzing a gaseous sample contained in a photoacoustic gas cell, said method comprising the steps of:
   a) pumping a pulsed pump and tunable seed lasers and generating laser oscillation of the said lasers;
   b) pumping optical parametric generator-optical parametric amplifier unit (OPG-OPA) with radiations of the pulsed pump and seed lasers and generating of tunable mid-IR signal and idler waves;
   c) directing a tunable laser radiation from said OPG-OPA to the gas cell and measuring absorption spectrum; and
   d) comparing the measured absorption spectrum with the known absorption spectra of the gaseous sample to determine the composition of the gaseous sample, and
   wherein step a) further includes: generating a Q-switched Holmium laser radiation as a pump source for said OPG-OPA.

8. A method for analyzing a gaseous sample contained in a photoacoustic gas cell, said method comprising the steps of:
   a) pumping a pulsed pump and tunable seed lasers and generating laser oscillation of the said lasers;
   b) pumping optical parametric generator-optical parametric amplifier unit (OPG-OPA) with radiations of the pulsed pump and seed lasers and generating of tunable mid-IR signal and idler waves;
   c) directing a tunable laser radiation from said OPG-OPA to the gas cell and measuring absorption spectrum; and
   d) comparing the measured absorption spectrum with the known absorption spectra of the gaseous sample to determine the composition of the gaseous sample;
   wherein
      step a) further includes: generating a Q-switched Erbium laser radiation as a pump source for said OPG-OPA, and
      step b) further comprises the step of
         providing a ZGP nonlinear crystal in said OPG-OPA generating radiation over the 2-10 µm mid-IR spectral range,
         rotating the position of said ZGP nonlinear crystal with a ZGP stepping motor,
         providing a wavelength controller connected with a ZGP stepping motor,
         calculating the required angle of rotation of the ZGP for the current wavelength, and
         rotating the ZGP according to calculations.

9. A method for analyzing a gaseous sample contained in a photoacoustic gas cell, said method comprising the steps of:
   a) pumping a pulsed pump and tunable seed lasers and generating laser oscillation of the said lasers;
   b) pumping optical parametric generator-optical parametric amplifier unit (OPG-OPA) with radiations of the pulsed pump and seed lasers and generating of tunable mid-IR signal and idler waves;
   c) directing a tunable laser radiation from said OPG-OPA to the gas cell and measuring absorption spectrum; and
   d) comparing the measured absorption spectrum with the known absorption spectra of the gaseous sample to determine the composition of the gaseous sample;
   wherein step a) further comprises:
      generating a single frequency tunable $Cr^{2+}$:II-VI laser radiation using a $Cr^{2+}$:II-VI master oscillator and $Cr^{2+}$:II-VI a power amplifier, where II-VI stands for Zn, Se, CdSe, ZnS, and their mixtures, and
      transmitting said $Cr^{2+}$:II-VI widely tunable seed laser radiation to said OPG-OPA wherein said $Cr^{2+}$:II-VI widely tunable seed laser radiation is continuously tunable over a 2-3.5 µm spectral range.

10. A method for analyzing a gaseous sample contained in a photoacoustic gas cell, said method comprising the steps of:
   a) pumping a pulsed pump and tunable seed lasers and generating laser oscillation of the said lasers;
   b) pumping optical parametric generator-optical parametric amplifier unit (OPG-OPA) with radiations of the pulsed pump and seed lasers and generating of tunable mid-IR signal and idler waves;
   c) directing a tunable laser radiation from said OPG-OPA to the gas cell and measuring absorption spectrum; and
   d) comparing the measured absorption spectrum with the known absorption spectra of the gaseous sample to determine the composition of the gaseous sample, and wherein step b) further comprises the step of providing a ZGP nonlinear crystal in said OPG-OPA generating radiation over the 2-10 μm mid-IR spectral range;

rotating the position of said ZGP nonlinear crystal with a ZGP stepping motor;

providing a wavelength controller connected with a ZGP stepping motor;

calculating the required angle of rotation of the ZGP for the current wavelength; and rotating the ZGP according to calculations.

11. An optical nose system having a broadly tunable, narrow linewidth mid-IR laser source wherein the laser source has a modular structure and comprises a) a tunable seed laser unit including a single-longitudinal mode, widely tunable $TM^{2+}$:II-VI master oscillator with a $TM^{2+}$:II-VI power amplifier having a laser output, where $TM^{2+}$ stands for transition metal ion selected from the group consisting of $Cr^{2+}$, $Fe^{2+}$, $Co^{2+}$ and $Ni^{2+}$, and II-VI stands for ZnS, ZnSe, CdS, CdSe, ZnTe, CdTe and their mixtures;

b) a pulsed pump laser unit including a single-frequency, high energy, Q-switch laser having a laser output; and, c) an Optical Parametric Generator-Amplifier, pumped by said pulsed pump laser unit and seeded by said seed tunable laser unit having a mid-IR output selectively variable over about 2 to 20 μm, and wherein said Optical Parametric Generator-Amplifier is a difference frequency generator device where the laser radiations from the seed tunable laser unit and a high power pump laser unit are mixed in nonlinear crystal, selected from the group of ZGP, CdSe or GaSe.

12. The optical nose system as defined in claim 11, further comprising a photo-acoustic cell receiving an optical input from said Optical Parametric Generator-Amplifier for analyzing a gaseous sample.

* * * * *